(12) United States Patent
Morita

(10) Patent No.: US 8,840,559 B2
(45) Date of Patent: Sep. 23, 2014

(54) ORGANIC PIEZOELECTRIC MATERIAL, ULTRASONIC OSCILLATOR USING THE MATERIAL, METHOD FOR MANUFACTURING THE ULTRASONIC OSCILLATOR, ULTRASONIC PROBE, AND ULTRASONIC MEDICAL DIAGNOSTIC IMAGING DEVICE

(75) Inventor: Kiyokazu Morita, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 754 days.

(21) Appl. No.: 12/921,175

(22) PCT Filed: Mar. 4, 2009

(86) PCT No.: PCT/JP2009/054055
§ 371 (c)(1),
(2), (4) Date: Sep. 7, 2010

(87) PCT Pub. No.: WO2009/113432
PCT Pub. Date: Sep. 17, 2009

(65) Prior Publication Data
US 2011/0021916 A1 Jan. 27, 2011

(30) Foreign Application Priority Data

Mar. 14, 2008 (JP) .................... 2008-065534

(51) Int. Cl.
*A61B 8/00* (2006.01)
*C08G 18/76* (2006.01)
*B06B 1/06* (2006.01)
*H01L 41/193* (2006.01)
*C08G 18/32* (2006.01)
*H01L 41/45* (2013.01)
*C08G 18/38* (2006.01)

(52) U.S. Cl.
CPC ............... *A61B 8/00* (2013.01); *A61B 8/4483* (2013.01); *C08G 18/7692* (2013.01); *B06B 1/06* (2013.01); *H01L 41/193* (2013.01); *C08G 18/3271* (2013.01); *H01L 41/45* (2013.01); *A61B 8/4405* (2013.01); *C08G 18/3814* (2013.01)
USPC .......... 600/459; 73/584; 310/311; 252/62.9 R

(58) Field of Classification Search
USPC ................................................... 252/62.9 R
See application file for complete search history.

(56) References Cited

U.S. PATENT DOCUMENTS 4,405,402 A * 9/1983 Quilliam .................... 156/273.7
5,064,783 A * 11/1991 Luckevich ..................... 501/12
2006/0057361 A1* 3/2006 Ounaies et al. .............. 428/323

FOREIGN PATENT DOCUMENTS

JP 59-027584 2/1984
JP 02284485 11/1990

(Continued)

OTHER PUBLICATIONS

Uchino et al. "Introduction to Piezoelectric Actuators and Transducers". International Center for Actuators and Transducers. Jun. 2003.*

(Continued)

*Primary Examiner* — Unsu Jung
*Assistant Examiner* — Phong K Huynh
(74) *Attorney, Agent, or Firm* — Lucas & Mercanti, LLP

(57) ABSTRACT

Provided is an organic piezoelectric material which has excellent piezoelectric property, heat resistance property in particular. An ultrasonic oscillator, which is to be used for an ultrasonic medical diagnostic imaging device which can receive high frequencies at high sensitivity and is suitable for harmonic imaging techniques, a method for manufacturing such oscillator, and an ultrasonic probe are also provided. The ultrasonic medical diagnostic imaging device is provided by sing such oscillator, method and probe. The organic piezoelectric material is characterized by containing empty particles having an average particle diameter of 10 μm or less.

10 Claims, 3 Drawing Sheets

(56) References Cited

FOREIGN PATENT DOCUMENTS

| | | |
|---|---|---|
| JP | 05-283272 | 10/1993 |
| JP | 05311399 | 11/1993 |
| JP | 6216422 | 8/1994 |
| JP | 06-342947 | 12/1994 |
| JP | 07-297461 | 11/1995 |
| JP | 11276478 | 10/1999 |
| JP | 2002209292 | 7/2002 |
| JP | 2007145960 | 6/2007 |
| JP | 2007222605 | 9/2007 |
| JP | 2008-036202 | 2/2008 |
| JP | 200847693 | 2/2008 |

OTHER PUBLICATIONS

Japanese Office Action, Patent Application No. 2010-502781, date of drafting Apr. 24, 2013.

English translation of Japanese Office Action, Patent Application No. 2010-502781, date of drafting Apr. 24, 2013.

Japanese Office Action, Notice of Reasons for Refusal, Patent Appln. #2010-502781, date mailed: Aug. 13, 2013 (3 pages).

English translation of Japanese Office Action, Notice of Reasons for Refusal, Patent Appln. #2010-502781, date mailed: Aug. 13, 2013 (4 pages).

Jspanese Office Action, Examiner's Decision of Refusal, Patent Application No. JP2010-502781, drafting date: Dec. 5, 2013. Date mailed: Dec. 10, 2013 (2 pages).

English translation of Jspanese Office Action, Examiner's Decision of Refusal, Patent Application No. JP 2010-502781, drafting date: Dec. 5, 2013. Date mailed: Dec. 10, 2013 (2 pages).

* cited by examiner

ORGANIC PIEZOELECTRIC MATERIAL, ULTRASONIC OSCILLATOR USING THE MATERIAL, METHOD FOR MANUFACTURING THE ULTRASONIC OSCILLATOR, ULTRASONIC PROBE, AND ULTRASONIC MEDICAL DIAGNOSTIC IMAGING DEVICE

This is a 371 of PCT/JP2009/054055 filed Mar. 4, 2009 which in turn claimed the priority of Japanese Patent Application No. 2008-065534 filed Mar. 14, 2008, both applications are incorporated by reference herein.

TECHNICAL FIELD

The present invention relates to an organic piezoelectric material, an ultrasonic oscillator suitable for a high frequency and broadband range using the same, a method for producing the ultrasonic oscillator, an ultrasonic probe, and an ultrasonic medical diagnostic imaging device.

BACKGROUND

Usually, ultrasonic waves are collectively referred to as sound waves of at least 16,000 Hz and can inspect the interior nondestructively and harmlessly, having thereby been applied to various fields such as defect inspection and disease diagnosis. One of these is an ultrasonic diagnostic system in which the interior of a tested subject is scanned with an ultrasonic wave, and then based on a received signal generated from a reflective wave (echo) of the ultrasonic wave from the interior of the tested subject, an image of the interior state in the tested subject is formed. In such an ultrasonic diagnostic system, an ultrasonic probe to transmit and receive an ultrasonic wave with respect to a tested subject is used. As this ultrasonic probe, an ultrasonic transmitting and receiving element constituted of a oscillator is used in which an ultrasonic wave is generated via mechanical vibration based on a transmitting signal, and a received signal is generated by receiving a reflective signal of the ultrasonic wave generated based on the difference in acoustic impedance within a tested subject.

In recent years, a harmonic imaging technology has been studied and developed to form an image of the interior state within a tested subject, not based on a frequency (basic frequency) component of an ultrasonic wave having been transmitted into the tested subject interior from an ultrasonic probe, but based on its harmonic frequency component. Such a harmonic imaging technology has various advantages as follows: (1) the sidelobe level is smaller than the level of a basic frequency component and the S/N ratio (signal to noise ratio) is improved, whereby contrast resolution is enhanced; (2) higher frequency is realized and then beam width becomes narrowed, whereby lateral resolution is enhanced; (3) in a close range, sound pressure is small and also sound pressure variation is minimal, whereby multiple reflection is inhibited; and (4) the attenuation beyond the focus is comparable to that of a basic wave and a larger deep velocity is realized compared with the case of use of a high frequency as the basic wave. For an ultrasonic probe used in such harmonic imaging, a broad frequency band is required ranging from the frequency of a basic wave to the frequency of a harmonic. The frequency range of the low frequency side is used for transmission to transmit the basic wave. In contrast, the frequency range of the high frequency side is used for reception to receive the harmonic (for example, refer to Patent Document 1).

The ultrasonic probe disclosed in Patent Document 1 is an ultrasonic probe which is applied to a tested subject to transmit ultrasonic waves into the tested subject and to receive the ultrasonic waves having been returned via reflection within the tested subject. This ultrasonic probe has a first piezoelectric layer containing a plurality of arranged first piezoelectric elements with a predetermined first acoustic impedance to transmit a basic wave having ultrasonic waves of a predetermined central frequency toward the interior of a tested subject and to receive the basic wave among the ultrasonic waves having been returned via reflection within the tested subject, and further has a second piezoelectric layer containing a plurality of arranged piezoelectric elements with a second acoustic impedance, which is smaller than the first acoustic impedance, to receive a harmonic among the ultrasonic waves having been returned via reflection within the tested subject. Herein, the second piezoelectric layer is entirely layered on the first piezoelectric layer on the side in which this ultrasonic probe is applied to the tested subject. Therefore, the ultrasonic probe can transmit and receive ultrasonic waves in a broad frequency band with such a constitution. For a basic wave in harmonic imaging, a sound wave having as narrow a band width as possible is preferable. As a piezoelectric body playing such a role, a single crystal such as crystal, $LiNbO_3$, $LiTaO_3$, or $KNbO_3$; a thin film such as ZnO or AlN; and a so-called inorganic piezoelectric material obtained by polarization treatment of a fired body such as a $Pb(Zr,Ti)O_3$ based body are widely used. These piezoelectric materials of inorganic materials have features such as high elasticity stiffness and mechanical loss coefficient, as well as high density and dielectric constant. On the other hand, for a piezoelectric element to detect received waves of the high frequency side, sensitivity is required in a broader band width. Therefore, these inorganic materials are unsuitable.

As a piezoelectric element suitable in the high frequency and broadband range, an organic piezoelectric material employing an organic polymer substance is known. There have been developed organic piezoelectric materials such as, for example, polyvinylidene fluoride (hereinafter referred to as "PVDF"), polyvinylidene cyanide (hereinafter referred to as "PVDCN"), and a polyurea resin containing a ureine group obtained from a diisocyanate compound such as 4,4'-diphenylmethane diisocyanate (MCI) and a diamine compound such as 4,4'-diaminodiphenylmethane (MDA) (refer to Patent Documents 2-4). These organic piezoelectric materials exhibit excellent processability such as thinner layer formation and larger area formation, being able to produce any appropriate shape and configuration. These materials have features such as small elastic modulus and dielectric constant, producing whereby features enabling high sensitivity detection in view of use as a sensor.

However, when an ultrasonic probe is formed using any of these organic piezoelectric materials, piezoelectric characteristics are inadequate, and especially in high temperatures, its physical properties such as piezoelectric characteristics and elasticity stiffness tend to decrease to a large extent. Therefore, there have been noted problems such that the applicable temperature range is limited; and piezoelectricity is impaired and deformation is produced by heating during production.

Patent Document 1: Unexamined Japanese Patent Application Publication (hereinafter referred to as JP-A) No. 11-276478
Patent Document 2: JP-A No. 6-216422
Patent Document 3: JP-A No. 2-284485
Patent Document 4: JP-A No. 5-311399

DISCLOSURE OF THE INVENTION

Problems to be Solved by the Invention

In view of the above problems and circumstances, the present invention was completed. An object to solve these problems is to provide an organic piezoelectric material exhibiting excellent piezoelectric characteristics, and specifically exhibiting excellent heat resistance. Further, the object is to provide an ultrasonic oscillator, capable of receiving high-frequency waves with high sensitivity, used in an ultrasonic medical diagnostic imaging device suitable for the harmonic imaging technology; a method for producing the ultrasonic oscillator; and an ultrasonic probe. Still further, thereby, the object is to provide an ultrasonic medical diagnostic imaging device.

Means to Solve the Problems

The above-described problems relating to the present invention are resolved by the following means.
1. An organic piezoelectric material comprising hollow particles having an average particle diameter of 10 μm or less.
2. The organic piezoelectric material of the above-described item 1, wherein an electromechanical coupling coefficient thereof is 0.3 or more.
3. An ultrasonic oscillator produced with the organic piezoelectric material of the above-described items 1 or 2.
4. A method for producing the ultrasonic oscillator of the above-described item 3, wherein polarization treatment is carried out to the organic piezoelectric material of the above-described items 1 or 2 at one of the moments of:

before providing two electrodes on both surfaces of the organic piezoelectric material;

after providing one of the two electrodes on one of the surfaces of the organic piezoelectric material; and after providing the two electrodes on the both surfaces of the organic piezoelectric material.
5. The method for producing the ultrasonic oscillator of the above-described item 4, wherein the polarization treatment is a voltage applying treatment or a corona discharge treatment.
6. An ultrasonic probe comprising an ultrasonic emitting oscillator and an ultrasonic receiving oscillator, wherein an ultrasonic oscillator produced using the organic piezoelectric material of the above-described items 1 or 2 is used for the ultrasonic emitting oscillator or for the ultrasonic receiving oscillator.
7. An ultrasonic medical diagnostic imaging device comprising:

an electric signal generating means;

an ultrasonic probe provided with a plurality of oscillators which emit an ultrasonic wave to a tested subject after receiving the electric signal, and produce a received signal corresponding to a reflected wave from the tested subject; and an image processing means which produces an image of the tested subject by using the received signal produced by the ultrasonic probe, wherein the ultrasonic probe is provided with an ultrasonic emitting oscillator and an ultrasonic receiving oscillator, and at least one of the ultrasonic emitting oscillator and the ultrasonic receiving oscillator is an ultrasonic oscillator produced with the organic piezoelectric material of the above-described items 1 or 2.

Effects of the Invention

According to the above methods of the present invention, an organic piezoelectric material exhibiting excellent piezoelectric characteristics, and specifically exhibiting excellent heat resistance can be provided. Further, there can be provide an ultrasonic oscillator, capable of receiving high-frequency waves with high sensitivity, used in an ultrasonic medical diagnostic imaging device suitable for the harmonic imaging technology; a method for producing the ultrasonic oscillator; and an ultrasonic probe. Still further, an ultrasonic medical diagnostic imaging device can be provided using the same.

DESCRIPTION OF THE ALPHANUMERIC DESIGNATIONS

Figure 1:
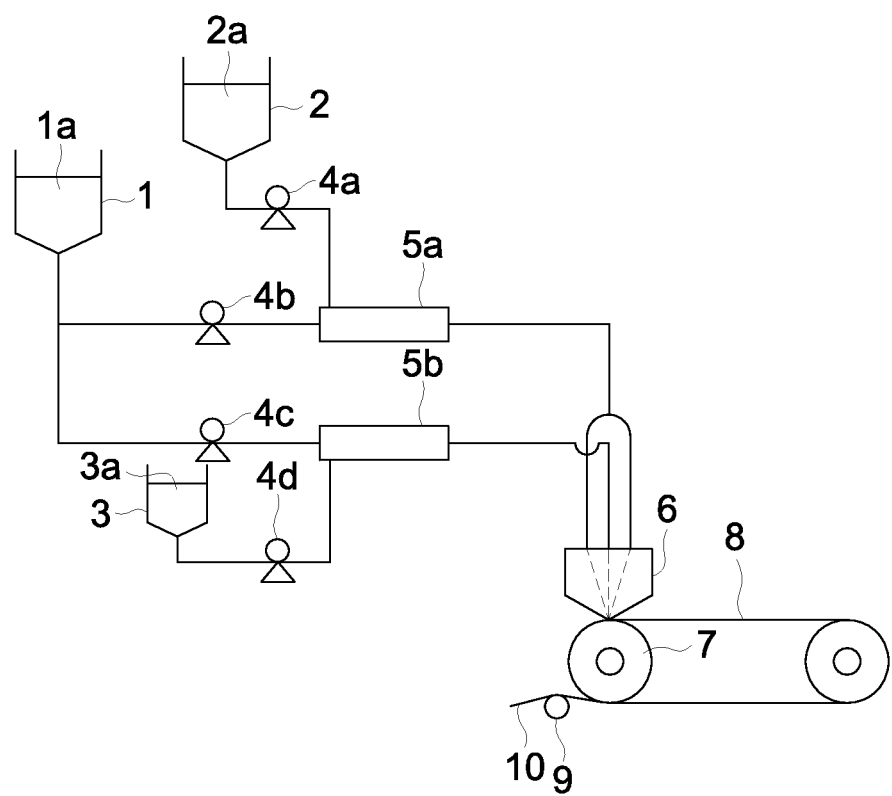
FIG. 1 is a process chart showing one example of a production apparatus for the organic piezoelectric material of the present invention.

1: organic piezoelectric material liquid tank
1a: organic piezoelectric material liquid
2: particle added liquid tank
2a: particle added liquid
3: additive liquid tank
3a: additive liquid
4a, 4b, 4c, and 4d: pumps
5a and 5b: in-line mixers
6: slit die
7: drum
8: casting belt
9: roller
10: organic piezoelectric material
P1: receiving piezoelectric material (film)
P2: support
P3: transmitting piezoelectric material (film)
P4: backing layer
P5: electrode
P6: acoustic lens
S: ultrasonic medial diagnostic imaging device
S1: ultrasonic medial diagnostic imaging device body
S2: ultrasonic probe
S3: operation input section
S4: display section

BEST EMBODIMENTS TO CARRY OUT THE INVENTION

The organic piezoelectric material of the present invention is characterized by containing hollow particles having an average particle diameter of 10 μm or less. This feature is a common technical feature of the embodiments of the present invention described in the above-described items 1 to 7.

From the viewpoint of solving the above problems of the present invention, the preferred embodiment of the present invention is an embodiment in which the electromechanical coupling coefficient of the organic piezoelectric material is preferably at least 0.3. Herein, the "electromechanical coupling coefficient" refers to one of the coefficients expressing piezoelectric characteristics, representing a ratio at which a piezoelectric body mutually converts electrical energy and mechanical energy. And the coefficient is also referred to as the coupling factor. With regard to the electromechanical coupling coefficient, the square of its magnitude is defined as energy dynamically stored with respect to an electrical input energy or energy electrostatically stored with respect to a dynamic input energy. This is a fundamental physical quantity which represents characteristics as an energy oscillator, providing also an indication of energy conversion, as well as being widely used as an evaluation value of fundamental characteristics of a piezoelectric body.

The organic piezoelectric material of the present invention has features of excellent piezoelectric characteristics and heat resistance, being whereby suitable for a material to form an organic piezoelectric film. Further, the organic piezoelectric film can suitably be used for an ultrasonic oscillator. Especially, in an ultrasonic probe having an ultrasonic transmitting oscillator and an ultrasonic receiving oscillator, the above film can suitably be used as an ultrasonic transmitting oscillator or an ultrasonic receiving oscillator. Further, this ultrasonic probe can be used for an ultrasonic medical diagnostic imaging device. The use as the above ultrasonic probe can preferably be realized in an ultrasonic medical diagnostic imaging device, for example, having a member to generate an electrical signal; an ultrasonic probe with a plurality of arranged oscillators to receive the electrical signal and to transmit ultrasonic waves toward a tested subject, as well as generating a received signal based on a reflective wave having been received from the tested subject; and an image processing member to form an image of the tested subject based on the received signal having been generated by the ultrasonic probe.

The present invention, constituent elements thereof, and the preferred embodiment to carry out the present invention will now be detailed.

(Organic Piezoelectric Materials)

The organic piezoelectric material of the present invention is characterized by being formed by simultaneously laminating films of at least 2 layers. An organic polymer material can suitably be employed for such an organic piezoelectric material. Further, when the organic polymer material is used to form an organic piezoelectric material, particles and appropriate other materials also can be mixed for the intended purpose.

<Hollow Particles>

The hollow particles concerning the present invention may have a structure where one large void is formed in the inner part of the particle. They may have a structure where a plurality of voids is formed in the inner part of the particle, and a plurality of small voids may be further formed in the inner part resulting in forming a sponge-like structure. Moreover, when the inner part of the above-mentioned hollow particles is sponge-like, each void may be independent or may be communicated with each other, and these may be mixed. The porosity of the above-mentioned hollow particles is preferably 10% or more. Here, the porosity means the ratio of the volume occupied by the porous part to the whole volume of the above-mentioned hollow particles. This porosity of the hollow particles is obtained by the observation of a particle section with a transmission electron microscope (TEM) and by measuring the specific gravity of the particles, for example.

As a material which constitutes the above-mentioned hollow particles, an inorganic material and an organic material are cited.

As hollow particles of an inorganic material, for example, silica, ceramic, volcanic ash (Shirasu), fly ash, alumina silicate ceramic and glass are cited. Among them, the silica hollow particles are preferable since the dielectric constant of a shell part will become to 3.8.

A preparation method is disclosed in JP-A No. 6-91194. With this method, an organosilicate compound such as methoxy silicate or ethoxy silicate is mixed sprayed with a forming agent, subsequently it is hydrolyzed to obtain a hollow silica powder. Another preparation method is disclosed in Japan Patent No. 2590428. With this method, after partial hydrolysis is carried out by adding alcohol, water, and an acid catalyst to tetraethyl orthosilicate, dibutyl phthalate is added to them, then the solution is mixed with stirring in an aqueous ammonia solution which contains a surfactant to emulsify. And a polycondensation reaction is allowed to take place to obtain spherical hollow-porous-silica particles. Another preparation method is disclosed in JP-A No. 11-29318. With this method, micron-sized spherical silica is prepared from tetraalkoxy silane and water by hydrolysis and polycondensation reaction. The micron-sized hollow spherical silica particles are provided with a shell having a gradient structure which is dense in the outer portion and rough in the inner portion. They are produced by making use of an interface reaction which deposit silica at an interface of gas-liquid or liquid-liquid (aqueous phase-oil phase). The obtained silica hollow particles are spherical and have a size of a micron order. Moreover, there is disclosed a method in JP-A No. 2005-263550. In this method, calcium carbonate is used as a template, after the surface of the template is covered with silica by hydrolysis of silicon alkoxide, calcium carbonate is dissolved by an acid treatment. By this method, hollow particles of silica nanometric size are obtained. Although any particles prepared by any one of the above-described methods can be suitably used, the preferable particles are those having a size of 10 μm or less.

The following can be cited as hollow particles of an organic material: polystyrene resin, acrylic resin, styrene acrylic resin, polyethylene resin, polypropylene resin, polyacetal resin, chlorinated polyether resin, polyvinyl chloride resin. Furthermore, the following are also cited: phenol-formaldehyde resin, urea-formaldehyde resins, melamine-formaldehyde resin, furan resin and unsaturated polyester resin prepared by addition polymerization.

Specific examples thereof are: polystyrene, poly-α-methylstyrene, poly-β-methylstyrene, poly(methyl methacrylate), poly(ethyl methacrylate), poly(isopropyl methacrylate), poly(isobutyl methacrylate), polyacrylonitrile, polymethacrylonitrile, polyvinylchloride, polytetrafluoroethylene, polyvinylalkohol, poly-o-vinylbenzyl alcohol, poly-m-vinylbenzyl alcohol, poly-p-vinylbenzyl alcohol, poly(vinyl formal), poly(vinyl acetal), poly(vinyl propional), poly(vinyl butyral), poly(vinyl isobutyral), poly(vinyl tertiary butyl ether), poly(vinyl pyrrolidone), poly(vinyl carbazole,) cellulose acetate, cellulose triacetate and polycarbonate.

Moreover, there can be used particles having a shell prepared with a copolymer obtained by various monomers. In addition, these resins may be the hollow particles having a multilayer structure. The hollow particles which are formed with these thermoplastic resins as a shell are not limited by the production method.

Among these hollow particles, preferable particles are made of styrene-acryl resin, polystyrene resin and acrylic resin which are cross-linked. Especially, the hollow polymer particles made of polystyrene/poly(meth)acrylate ester system polymer which form a multilayer structure are preferable, since a high porosity can be obtained. The shape of the hollow polymer particles is preferably spherical in appearance. The shape can be determined in detail by the form acquired with an electron microscope photograph and it is especially regarded as an ellipse form. The shape having an eccentricity of 0.9 or less is regarded as almost spherical.

Although the porosity (the ratio of the volume occupied by the porous part to the whole volume of the hollow particles) of the hollow particles used for the present invention is not limited in particular, the porosity is preferably 10% or more. More preferably, it is 30% or more. When the porosity is too small, the improvement effect of the physical-properties with respect to piezoelectricity will become insufficient. It is thought that the above-mentioned improvement effect becomes large when the porosity is large, but it is practically difficult to produce the hollow particles having a porosity of 90% or more.

In the present invention, the average particle diameter of hollow particles is 0.01 to 10 μm. Preferably, it is 0.2 to 8 μm or more, and more preferably, it is 0.5 to 5 μm.

In addition, it may be used together two or more sorts of hollow particles which have a different average particle diameter. In this case, the average particle diameter of the small hollow particles is preferably ½ or less than the average particle diameter of the large hollow particles, it is more preferable that the average particle diameter of the small hollow particles is ¼ or less than the average particle diameter of the large hollow particles. As for the above-mentioned hollow particles, it is desirable that the CV value of the particles is 20% or less from the viewpoints of prevention of dielectric breakdown during the polarization treatment. In addition, the CV value of the above-mentioned particle diameter can be calculated with the following scheme.

$CV$ value (%) of particle diameter=(Standard deviation of particle diameter/Average particle diameter)×100.

Here, the average particle diameter of the hollow particles indicates a diameter of a circle (equivalent circle diameter) which has an area equal to each particle image of hollow particles observed with the transmission electron microscopy.

The following way is cited as a measuring method of the average particle diameter of hollow particles. First, an organic piezoelectric material is applied on a base support such as PET, then it is inserted into a suitable folder, and the ultra-thin section having a thickness of 0.1 to 0.2 μm is prepared using a diamond knife in the direction substantially vertical to the surface of the base support. The produced ultra-thin section is transferred on a carbon film which has been supported by a copper mesh and hydrophilization has been carried out with glow discharge, then while cooling at less than −130° C. with liquid nitrogen it is observed with a transmission electron microscope (hereafter it is called as TEM). A magnification ratio of 5,000 to 40,000 is applied and the light-filed image is observed and it is recorded on a recording film, an imaging plate or on a CCD camera. In this case, it is required to taka a picture including the interface of the base support and the photosensitive layer so that the direction along the base support surface with respect to the flame of a recording medium in each picture image can be distinguished. Moreover, it is preferable to suitably select the part which does not have a tear, slack, and bending in a cut piece as a view field for taking a picture.

It is preferable to use a carbon film which is supported on an organic layer such as very thin collodion film or a formvar film. It is preferable to use an independent carbon film which is obtained by dissolving the rock salt substrate on which a carbon film has been formed, or to use an independent carbon film obtained by removing the above-mentioned organic layer with an organic solvent or ion etching.

An acceleration voltage of TEM is preferably from 80 to 400 kV, and it is more preferably from 80 to 200 kV. In addition, about the details of electron microscope observation technique and specimen production technique, "Japan Electron Microscopy Society, Kanto branch editing/Medicine and the biology electron microscope observing method" (Maruzen Co., Ltd.), and "Japan Electron Microscopy Society, Kanto branch editing/Electron microscope living specimen producing method" (Maruzen Co., Ltd.) can be referred to, respectively. As for the TEM picture image recorded on a suitable media, it is preferable to decompose into at least 1024 pixels×1024 pixels or more preferably into 2048 pixels×2048 pixels or more per one picture image, and to perform the image processing by a computer. In order to perform an image processing it is preferable to convert the analogue image recorded on a film into a digital image with a scanner etc., and to give shading correction and contrast edge enhancement if needed. It is required to align the longitudinal direction of the digital image frame with the direction of an interface of an optical photosensitivity layer with a base support in this case. Then, a histogram is created, after extracting the part which corresponds to particles with binarization processing, each one pixel of all directions is eroded, and the particle silhouette which has been touched is separated. Next, the direction of the maximum length and the shortest length are measured to each separated silhouette. An average particle diameter is calculated from the values obtained from at least 500, more preferably 1,000 silhouettes. When measuring with the above-mentioned process, it is preferable to fully rectify the length correction per pixel (scale correction) and the two-dimensional strain of an instrumentation system beforehand using a standard reference. Uniform latex particles (DULP) marketed from the U.S. Dow Chemical Co. can be suitably used as a standard reference. It is preferable to use polystyrene particles which have less than 10% of coefficient of variation with respect to the particle diameter of 0.1 to 0.3 μm. Specifically, a lot of the particle diameter of 0.212 μm and the standard deviation of 0.0029 μm can be obtained.

The details of an image processing technique can be referred to "Edited by Hiroshi Tanaka: Image processing application technology (Kogyo Chosakai Publishing)." As an image processing program or apparatus, although they are not specifically limited as long as the above-mentioned processes can be made, but Luzex-III by Nireco Corp. is cited as an example.

In the present invention, it is preferable that the dielectric constant of the component which constitutes the shell part of hollow particles is 8 or less. Although the reason is unknown, when a material of a good insulating property with a low dielectric constant is used for a shell part, the improvement effect of piezoelectric property tends to be large. In order to satisfy the above-mentioned requirements, as a material which constitutes hollow particles, it is preferable to use an organic material.

Moreover, the organic piezoelectric material of the present invention is characterized in that it contains hollow particles having an average particle diameter of 10 μm or less in an amount of 0.1 to 99.9 weight % of, when the total mass is made into 100%. The above-mentioned content is preferably 10 to 50%.

As a way of manufacturing the above-mentioned hollow particles, it is not limited in particular, but they can be produced by a well-known manufacturing way. Examples of a manufacturing way include: a mini emulsion polymerization method, an emulsion polymerization method, a phase inversion emulsion polymerization method, a micro suspension polymerizing method, a suspension polymerization method, a dispersion polymerizing method, a seed polymerization method and a soap free precipitation polymerizing method. Among them, a mini emulsion polymerization method or a seed polymerization method is suitably used since it is excellent in controlling a hollow ratio. Moreover, the materials marketed can also be used as hollow particles. For example, it can be manufactured in accordance with the way disclosed in JP-A No. 64-1704, JP-A No. 5-279409, JP-A No. 6-248012 and JP-A No. 10-110018, using a monomer containing an acidic group and another monomer which can copolymerize with this monomer.

As a way of preparing a dispersion liquid of the hollow particles concerning the present invention, for example, three kinds of methods shown below are cited.

(Preparation Method A)

A solvent and hollow particles are stirred and mixed and then dispersed using a homogenizer. The resulting product is designated as a hollow particle dispersion. The hollow particle dispersion is added to an organic piezoelectric material liquid and the resulting mixture is stirred.

(Preparation Method B)

A solvent and hollow particles are stirred and mixed and then dispersed using a homogenizer. The resulting product is designated as a hollow particle dispersion. Separately, a small amount of an organic piezoelectric material (for example, PVDF, polyurea resin, or polythiourea resin) is added to a solvent and the resulting mixture was dissolved with stirring. The above hollow particle dispersion is added to the resulting product, followed by stirring. The resulting liquid is designated as a hollow particle added liquid. The hollow particle added liquid is sufficiently mixed with the organic piezoelectric material liquid using an in-line mixer.

(Preparation Method C)

A small amount of an organic piezoelectric material (for example, PVDF, polyurea resin, or polythiourea resin) is added to a solvent and the resulting mixture was dissolved with stirring. Hollow particles are added to the resulting product and dispersed using a homogenizer. The resulting liquid is designated as a hollow particle added liquid. The hollow particle added liquid is sufficiently mixed with the organic piezoelectric material liquid using an in-line mixer.

Preparation method A exhibits excellent hollow particle dispersibility and preparation method C is excellent in view of no tendency of re-aggregation of hollow particles. Preparation method B is excellent in view of both hollow particle dispersibility and no tendency of re-aggregation of hollow particles, resulting in a preferable preparation method which is excellent in both respects.

(Dispersion Method)

When hollow particles are mixed with a solvent and then dispersed, the concentration of the hollow particles is preferably 5-30% by mass, more preferably 10-25% by mass, most preferably 15-20% by mass. Larger dispersion concentration is preferable, since aggregates tend to be reduced.

As a solvent used, there is usable any of alcohols such as methyl alcohol or ethyl alcohol, ketones such as acetone or methyl ethyl ketone, aromatic hydrocarbons such as benzene, toluene, or xylene, dimethylformamide, dimethylacetamide, dimethyl sulfoxide, and N-methylpyrrolidone. Any of these solvents is preferably usable. However, of these, preferable is a solvent which dissolves an organic piezoelectric material to be used (for example, PVDF or a polyurea resin) at a concentration of 5% by mass or more.

When hollow particles are dispersed, it is preferable that the organic piezoelectric material coexists with the hollow particles, since dispersibility can be improved and the amount of aggregates can be reduced to result in preventing the aggregation of the hollow particles when mixing with the organic piezoelectric material. The hollow particles are preferably added to an organic piezoelectric material at 0.01-10% by mass (weight %) based on 100% by mass of the organic piezoelectric material, more preferably 0.05-3% by mass.

As the homogenizer, a common homogenizer can be used. The homogenizer is roughly divided into a media homogenizer and a medialess homogenizer. The medialess homogenizer is preferably used for dispersion of silicon dioxide particles since aggregates can be minimized.

The media homogenizer includes a ball mill, a sand mill, and a Dyno mill. The medialess homogenizer includes an ultrasonic type, a centrifugal type, and a high pressure type. Of these, in the present invention, a high pressure homogenizer is preferable. The high pressure homogenizer is an apparatus creating special conditions such as a high shear or high pressure state passing a composition prepared by mixing fine particle with a solvent through a narrow tube at high speed. In the case of treatment using such a high pressure homogenizer, for example, the maximum pressure condition within the apparatus is preferably at least $9.81 \times 10^6$ Pa (100 kgf/cm$^2$) in a narrow tube of a tube diameter of 1-2,000 μm, more preferably at least $1.96 \times 10^7$ Pa (200 kgf/cm$^2$). Further, in this case, those attaining a maximum attainable rate of at least 100 m/second and a heat transfer rate of at least 100 kcal/hour are preferable. Homogenizers as described above include an ultrahigh-pressure homogenizer (trade name: Microfluidizer, produced by Microfluidics Corp.) and Nanomizer (produced by Nanomizer Inc.), as well as Manton-Gaulin-type high pressure homogenizers such as a homogenizer produced by Izumi Food Machinery Co., Ltd. and UHN-01 (produced by Sanwa Machinery Co., Ltd.).

<Organic Polymer Material Constituting an Organic Piezoelectric Material>

As an organic polymer material (hereinafter also referred to as a "polymer material") serving as a constituent material of the organic piezoelectric material of the present invention, various organic polymer materials, having been conventionally used as a piezoelectric material, can be used.

For example, as a typical material, an organic polymer material containing vinylidene fluoride as a main component is usable from the viewpoint of excellent piezoelectric characteristics and easy availability.

Specifically, a homopolymer of polyvinylidene fluoride or a copolymer having vinylidene fluoride as a main component, which has a $CF_2$ group with a large dipole moment, is preferable.

Incidentally, as a second component of a copolymer, tetrafluoroethylene, trifluoroethylene, hexafluoropropane, or chlorofluoroethylene is usable.

For example, in the case of a vinylidene fluoride/trifluoroethylene copolymer, the electromechanical coupling coefficient of the thickness direction varies with the copolymerization ratio. Therefore, the copolymerization ratio of the former is preferably 60-99 mol %, more preferably 70-95 mol %.

Herein, a polymer formed from 70-95 mol % of vinylidene fluoride and 5-30 mol % of perfluoroalkyl vinyl ether, perfluoroalkoxyetylene, or perfluorohexaethylene can inhibit a transmitting basic wave and increase the sensitivity of harmonic reception in combination of a transmitting inorganic piezoelectric element with a receiving organic piezoelectric element.

The above polymer piezoelectric material is characterized by being formed into a thin film compared with an inorganic piezoelectric material formed of ceramics, being whereby able to be formed as a oscillator responding to transmission and reception of high-frequency waves.

In the present invention, other than the above polymer materials, various organic polymer materials can be used. Of these, preferable is an organic polymer material formed from a polymerizable compound having an electron attracting group acting to increase the dipole moment amount of the organic polymer material. Such an organic polymer material acts to increase the dipole moment amount, whereby in the case of use as an organic piezoelectric material (film), excellent piezoelectric characteristics can be realized.

In the present invention, "an electron withdrawing group" designates a group having a Hammett constant ($\sigma_p$) of 0.10 or more. A Hammett constant is a value indicating the degree of electron withdrawing property. Here, the values of Hammett constant $\sigma_p$ are preferably taken from the values described in the reports by Hansch, C. Leo, et al., (for example, J. Med. Chem., 16, 1207 (1973); and ibd. 20, 304 (1977)).

Examples of a group or an atom having the $\sigma_p$ value of 0.10 or more are: a halogen atom (a fluorine atom, a chlorine atom, a bromine atom and iodine atoms), a carboxyl group, a cyano group, a nitro group, a halogenated alkyl group (for example, trichloromethyl, trifluoromethyl, chloromethyl, trifluoromethylthiomethyl, trifluoromethanesulfonylmethyl and perfluorobutyl), an aliphatic, aromatic, or aromatic heterocyclic acyl group (for example, formyl, acetyl and benzoyl), an aliphatic, aromatic, or aromatic heterocyclic sulfonyl group (for example, trifluoromethanesulfonyl, methanesulfonyl and benzenesulfonyl), a carbamoyl group (for example, carbamoyl, methylcarbamoyl, phenylcarbamoyl and 2-chloro-phenylcarbamoyl), an alkoxycarbonyl group (for example, methoxycarbonyl, ethoxycarbonyl and diphenylmethylcarbonyl), a substituted aryl group (for example, pentachlorophenyl, pentafluorophenyl, 2,4-dimethanesulfonyl phenyl and 2-trifluoromethylphenyl), an aromatic heterocyclic group (for example, 2-benzoxazolyl, 2-benzthiazolyl, 1-phenyl-2-benzimidazolyl and 1-tetrazolyl), an azo group (for example, phenylazo), a ditrifluoromethylamino group, a trifluoromethoxy group, an alkylsulfonyloxy group (for example, methanesulfonyloxy), an acyloxy group (for example, acyloxy and benzoyloxy), an arylsulfonyloxy group (for example, benzenesulfonyloxy), a phosphoryl group (for example, dimethoxyphosphoryl, diphenylphosphoryl), and a sulfamoyl group (for example, N-ethyl sulfamoyl, N,N-dipropyl sulfamoyl, N-(2-dodecyloxyethyl)sulfamoyl, N-ethyl-N-dodecyl sulfamoyl and N,N-diethyl sulfamoyl).

As specific examples of the compound which can be used for the present invention, the following compounds or their derivatives can be cited. However, the examples are not limited to these. For example, a compound containing a urea bond which is formed by the reaction of a diamine compound described later with a diisocyanate compound containing a isocyanate group, and a compound containing a thiourea bond which is formed by the reaction of a diamine compound described later with a dithiocyanate compound containing a thioisocyanate group are cite.

Examples of a diamine compound are: 4,4'-diaminodiphenylmethane (MDA), 4,4'-methylenebis(2-methylaniline), 4,4'-methylenebis(2,6-dimethylaniline), 4,4"-methylenebis(2-ethyl-6-methylaniline), 4,4'-methylenebis(2,6-diethylaniline), 4,4'-methylenebis(2,6-di-t-butylaniline), 4,4'-methylenebis(2,6-dicyclohexylaniline), 4,4'-methylenebis(2-ethylaniline), 4,4'-methylenebis(2-t-butylaniline), 4,4'-methylenebis(2-cyclohexylaniline), 4,4'-methylenebis(3,5-dimethylaniline), 4,4'-methylenebis(2,3-dimethylaniline), 4,4'-methylenebis(2,5-dimethylaniline), 2,2-bis(4-aminophenyl)hexafluoropropane, 2,2-bis(4-aminophenyl)propane, 1,1-bis(4-aminophenyl)cyclohexane, α,α-bis(4-aminophenyl)toluene, 4,4'-methylenebis(2-chloroaniline), 4,4'-methylenebis(2,6-dichloroaniline), 4,4'-methylenebis(2,3-dibromoaniline), 3,4'-diaminodiphenyl ether, 4,4'-diaminooctafluorodiphenyl ether, 4,4'-diaminodiphenyl sulfide, 4,4'-diaminodiphenyl disulfide, bis(4-aminophenyl)sulfone, bis(3-aminophenyl)sulfone, bis(3-amino-4 hydroxyphenyl)sulfone, bis(4-aminophenyl)sulfoxide, 1,4-bis(4-aminophenoxy)benzene, 1,3-bis(4-aminophenoxy)benzene, 1,3-bis(3-aminophenoxy)benzene, 2,2-bis[(4-(4-aminophenoxy)phenyl)]propane, 2,2-bis[(4-(4-aminophenoxy)phenyl)]hexafluoropropane, 2,5-bis(4-aminophenyl)-1,3,4-oxadiazole, neopentyl glycol bis(4-aminophenyl)ether, 4,4'-diaminostilbene, α,α'-bis-(4-aminophenyl)-1,4-diisopropylbenzene, 1,2-phenylenediamine, 1,3-phenylenediamine, 1,4-phenylenediamine, benzidine, 4,4'-diaminooctafluoro biphenyl, 3,3'-diaminobenzidine, 3,3'-dimethylbenzidine, 2,2'-bis(trifluoromethyl)benzidine, 3,3', 5,5'-tetramethylbenzidine, 3,3"-dihydroxybenzidine, 3,3'-dimethylbenzidine, 3,3'-dihydroxy-5,5'-dimethylbenzidine, 4,4"-diamino-p-terphenyl, 1,5-diaminonaphthalene, 1,8-diaminonaphthalene, 2,3-diaminonaphthalene, 2,6-diaminonaphthalene, 2,7-diaminonaphthalene, 3,3'-dimethylnaphthidine, 2,7-diaminocarbazole, 3,6-diaminocarbazole, 3,4-diaminobenzoic acid, 3,5-diaminobenzoic acid, 1,5-diaminopentane, 1,6-diaminohexane, 1,7-diaminoheptane, 1,8-diaminooctane, 1,9-diaminononane, 1,5-dimethylhexylamine, 1,3-bis(aminomethyl)cyclohexane, 1,4-bis(aminomethyl)cyclohexane, 1-1:4,4'-diaminobenzophenone, 4,4'-dimethylamino-3,3"-dichlorobenzophenone, 4,4'-diamino-5,5'-diethyl-3,3'-difluorobenzophenone, 4,4'-diamino-3,3',5, 5'-tetrafluorobenzophenone, 2,2-bis(4-aminophenyl) propane, 2,2-bis(4-amino-3,5-dichlorophenyl)propane, 2,2-bis(4-aminophenyl)hexafluoropropane, 2,2-bis(4-amino-3-fluorophenyl)hexafluoropropane, 4,4'-diaminodiphenyl ether (ODA), 4,4'-diamino-3,3',5,5'-tetrachlorodiphenyl ether, 4,4'-diaminodiphenyl sulfide, 4,4'-diamino-3,3'-dibromodiphenyl sulfide, 4,4'-diaminodiphenyl disulfide, 4,4'-diamino-3,3',5,5'-tetrafluorodiphenyl disulfide, bis(4-aminophenyl)sulfone, bis(4-amino-3-chloro-5-methylphenyl) sulfone, bis(4-aminophenyl)sulfoxide, bis(4-amino-3-bromophenyl)sulfoxide, 1,1-bis(4-aminophenyl)cyclopropane, 1,1-bis(4-aminophenyl)cyclooctane, 1,1-bis(4-aminophenyl)cyclohexane, 1,1-bis(4-amino-3,5-difluorophenyl)cyclohexane, 4,4'-(cyclohexylmethylene)dianiline, 4,4'-(cyclohexylmethylene)bis(2,6-dichloroaniline), 2,2-bis(4-aminophenyl)diethyl malonate, 2,2-bis(4-amino-3-chlorophenyl)diethyl malonate, 4-(di p-aminophenyl methyl) pyridine, 1-(di-p-aminophenylmethyl)-1H-pyrrole, 1-(di-p-aminophenylmethyl)-1H-imidazole and 2-(di-p-aminophenyl methyl)oxazole, and derivatives thereof.

Examples of a diisocyanate compound which forms a compound containing a urea bond by reacting with the aforesaid diamine compound are: 4,4'-diphenylmethanediisocyanate (MDI), 4,4'-methylenebis(2,6-dimethylphenylisocyanate), 4,4'-methylenebis(2,6-diethylphenylisocyanate), 4,4'-methylenebis(2,6-di-t-butylphenylisocyanate), 4,4'-methylenebis(2,6-dicyclohexylphenylisocyanate), 4,4'-methylenebis(2-methylphenylisocyanate), 4,4'-methylenebis(2-ethylphenylisocyanate), 4,4'-methylenebis(2-t-butylphenylisocyanate), 4,4'-methylenebis(2-cyclohexylphenylisocyanate), 4,4'-methylenebis(3,5-dimethylphenylisocyanate), 4,4'-methylenebis(2,3-dimethylphenylisocyanate), 4,4'-methylenebis(2,5-dimethylphenylisocyanate), 2,2-bis(4-isocyanatophenyl) hexafluoropropane, 2,2-bis(4-isocyanatophenyl)propane, 1,1-bis(4-isocyanatophenyl)cyclohexane, α,α-bis(4-isocyanatophenyl)toluene, 4,4'-methylenebis(2,6-dichlorophenylisocyanate), 4,4'-methylenebis(2-chlorophenylisocyanate), 4,4'-methylenebis(2,3-dibromophenylisocyanate), m-xylylene diisocyanate, 4,4'-diisocyanato-3,3'-dimethylbiphenyl, 1,5-diisocyanatonaphthalene, 1,3-phenylene diisocyanate, 1,4-phenylene diisocyanate, 2,4-toluene diisocyanate (2,4-TDI), 2,6-toluene diisocyanate (2,6-TDI), 1,3-bis(2-isocyanato-2-propyl)benzene, 1,3-bis(isocyanatomethyl)cyclohexane, dicyclohexylmethane-4,4'-diisocyanate, isophorone diisocyanate, hexamethylene diisocyanate, trimethyl hexamethylene diisocyanate, 2,7-fluorene diisocyanate, benzophenone-4,4'-diisocyanic acid, 3,3'-dichlorobenzophenone-4,4'-diisocyanic acid, 5,5'-diethyl-3,3'-difluorobenzophenone 4,4'-diisocyanic acid, 2,2-bis(4-isocyanatophenyl)propane, 2,2-bis(3,5-dichloro-4-isocyanatophenyl)propane, 2,2-bis(4-isocyanatophenyl)hexafluoropropane, 2,2-bis(3-fluoro-4-isocyanatophenyl)hexafluoropropane, bis(4-isocyanatophenyl)ether, bis(3,5-difluoro-4-isocyanatophenyl)ether, bis(4-isocyanatophenyl)sulfide, bis(3,5-dibromo-4-isocyanatophenyl)sulfide, bis(4-isocyanatophenyl)disulfide, bis(4-isocyanatophenyl)sulfone, bis(4-isocyanatophenyl) sulfoxide, bis(3,5-difluoro-4-isocyanatophenyl)sulfoxide, 1,1-bis(4-isocyanatophenyl)cyclopropane, 1,1-bis(4-isocyanatophenyl)cyclooctane, 1,1-bis(4-isocyanatophenyl)cyclohexane, 1,1-bis(3,5-dichloro-4-isocyanatophenyl)cyclohexane, 4,4'-(cyclohexylmethylene)bis(isocyanatobenzene), 4,4'-(cyclohexylmethylene)bis(1-isocyanato-2-chlorobenzene), 2,2-bis(4-isocyanatophenyl)diethyl malonate, 2,2-bis(3-chloro-4-isocyanatophenyl)diethyl malonate, isocyanatophenylmethyl)pyridine, 1-(di p-isocyanatophenylmethyl)-1H-pyrrole, 1-(di-p-isocyanatophenylmethyl)-1H-imidazole, 2-(di-p-isocyanatophenylmethyl)oxazole, and derivatives thereof.

Examples of a diisothiocyanate compound which forms a compound containing a thiourea bond by reacting with the aforesaid diamine compound are: 4,4'-diphenylmethane diisothiocyanate, 4,4'-methylenebis(2,6-diethylphenylisothiocyanate), 4,4'-methylenebis(2,6-di-t-butylphenylisothiocyanate, 1,3-bis(isothiocyanatomethyl)cyclohexane, benzophenone-4,4'-diisothiocyanic acid, 3,3'-difluorobenzophenone 4,4'-diisothiocyanic acid, 2,2-bis(3,5-dichloro-4-isothiocyanatophenyl)propane, bis(4-isothiocyanatophenyl)ether, bis(4-isothiocyanatophenyl)sulfone, bis(4-isothiocyanatophenyl)sulfoxide, bis(3,5-difluoro-4-isothiocyanatophenyl)sulfoxide, 1,1-bis(4-isothiocyanatophenyl)cyclopropane, 1,1-bis(4-isothiocyanatophenyl)cyclooctane, 4,4'-(cyclohexylmethylene)bis(isothiocyanatobenzene), 2,2-bis(4-isothiocyanatophenyl)diethyl malonate, 1-(di-p-isothiocyanatophenylmethyl)-1H-pyrrole, 2-(di-p-isothiocyanatophenylmethyl)oxazole, and derivatives thereof.

Hereafter, organic polymer materials which can be used in the present invention will be described in more detail.

In the present invention, it is preferable that the organic polymer material which constitutes the organic piezoelectric material contains the compound which has a urea bond or a thiourea bond as a composition ingredient. The aforesaid compound is preferably formed by the compound represented by the following Formulas (1) to (3) or the derivative thereof as a raw material.

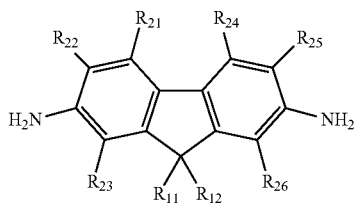

Formula (1)

(In Formula, $R_{11}$ and $R_{12}$ each independently represents a hydrogen atom, an alkyl group, a 3 to 10 membered non-aromatic cyclic group, an aryl group or a heteroaryl group, these groups may further have a substituent; and $R_{21}$ to $R_{26}$ each independently represents a hydrogen atom, an alkyl group, or an electron withdrawing group.)

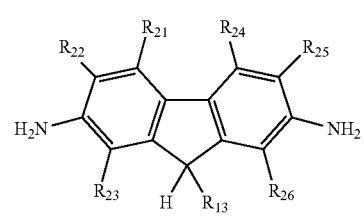

Formula (2)

(In Formula, $R_{13}$ each independently represents a carboxyl group, a hydroxyl group, a mercapto group, or an amino group, provided that an active hydrogen atom in these groups may be further substituted with an alkyl group, a 3 to 10 membered non-aromatic cyclic group, an aryl group, or a heteroaryl group, moreover, $R_{13}$ represents a carbonyl group, a sulfonyl group, a thiocarbonyl group, or a sulfonyl group, and these groups are bonded to a hydrogen atom, an aryl group, or a heteroaryl group; $R_{21}$ to $R_{26}$ each independently represents the same group as represented by $R_{21}$ to $R_{26}$ in the above-described Formula (1)).

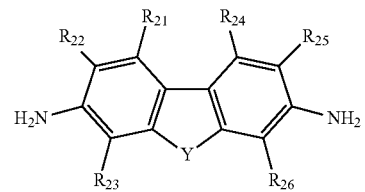

Formula (3)

(In Formula, Y each independently represents a keto group, an oxime group, or a substituted vinylidene group; and $R_{21}$ to $R_{26}$ each independently represents the same group as represented by $R_{21}$ to $R_{26}$ in the above-described Formula (1).)

Preferable examples are the compounds represented by the aforesaid Formulas (1) to (3), or the derivatives thereof.

<<Compounds Represented by Formula (1)>>

Examples of a compounds represented by Formula (1) are: 2,7-diaminofluorene, 2,7-diamino-4,5-dinitrofluorene, 2,7-diamino-3,4,5,6-tetrachlorofluorene, 2,7-diamino-3,6-difluorofluorene, 2,7-diamino-9-(n-hexyl)fluorene, 9,9-dimethyl-2,7-diaminofluorene, 2,7-diamino-9-benzylfluorene, 9,9-bisphenyl-2,7-diaminofluorene, 2,7-diamino-9-methylfluorene, 9,9-bis(3,4-dichlorophenyl)-2,7-diaminofluorene, 9,9-bis(3-methyl-4-chlorophenyl)-2,7-diaminofluorene, 9,9-bis(methyloxyethyl)-2,7-diaminofluorene and 2,7-diamino-3,6-dimethyl-9-aminomethylfluorene. However, the examples are not limited to the above-cited compounds.

<<Compounds Represented by Formula (2)>>

Examples of a compound represented by Formula (2) are: 2,7-diamino-9-fluorene carboxylic acid, 2,7-diamino-9-fluorene carboxyaldehyde, 2,7-diamino-9-hydroxyfluorene, 2,7-diamino-3,6-difluoro-9-hydroxyfluorene, 2,7-diamino-4,5-dibromo-9-mercaptofluorene, 2,7,9-triaminofluorene, 2,7-diamino-9-hydroxymethylfluorene, 2,7-diamino-9-(methyloxy) fluorene, 2,7-diamino-9-acetoxyfluorene, 2,7-diamino-3,6-diethyl-9-(perfluorophenyloxy)fluorene, 2,7-diamino-4,5-difluoro-9-(acetamide)fluorene, 2,7-diamino-isopropylfluorene-9-carboxyamide and 2,7-diamino-4,5-dibromo-9-methylsulfinylfluorene. However, the examples are not limited to the above-cited compounds.

<<Compounds Represented by Formula (3)>>

Examples of a compound represented by Formula (3) are: 9,9-dimethyl-2,7-diaminofluorenone, 2,7-diamino-9-benzyl fluorenone, 9,9-bisphenyl-2,7-diaminofluorenone, 2,7-diamino-9-methylfluorenone, 9,9-bis(3,4-dichlorophenyl)-2,7-diaminofluorenone, 9,9-bis(3-methyl-4-chlorophenyl)-2,7-diaminofluorenone, 9-hexylidene-2,7-diamino-4,5-dichlorofluorene, 1-(2,7-diamino-9-fluorenylidene)-2-phenylhydrazine and 2-(2,7-diamino-1,8-dimethyl-9-fluorenylidene)(methyl)pyridine. However, the examples are not limited to the above-cited compounds.

In the present invention, for example, after the aforesaid fluorenone compounds are allowed to react with a diol, a diamine, a diisocyanate, or a dithiocyanate in an aliphatic or an aromatic compound to prepare a polyurea or a polyurethane structure, the prepared compounds may be mixed with a compound represented by the following Formulas (4) to (6) or a high molecular weight compound derived therefrom so as to prepare a complex material.

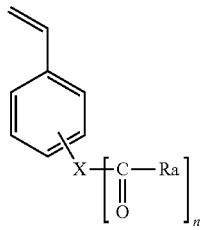

Formula (4)

(In Formula, Ra each independently represents a hydrogen atom, an alkyl group, an aryl group, an alkyl group containing an electron withdrawing group, an aryl group or a heteroaryl group containing an electron withdrawing group; X represents an atom which can be bonded, except for a carbon atom, or a single bond; and n represents an integer of not more than a value of an atomic valence of X minus 1.)

Examples of a compound represented by Formula (4) are: p-acetoxystyrene, p-acetylstyrene, p-benzoylstyrene, p-trifluoroacetylstyrene, p-monochloroacetylstyrene, p-(perfluorobutyryloxy)styrene, p-(perfluorobenzoyloxy)styrene, S-4-vinylphenylpyridine-2-carbothioate and N-(4-vinylphenyl)picolinamide. However, the examples are not limited to the above-cited compounds.

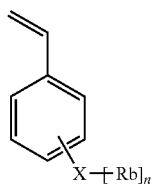

Formula (5)

(In Formula, Rb each independently represents an alkyl group containing an electron withdrawing group, an aryl group or a heteroaryl group containing an electron withdrawing group; X represents an atom which can be bonded, except for a carbon atom, or a single bond; and n represents an integer of not more than a value of an atomic valence of X minus 1.)

Examples of a compound represented by Formula (5) are: p-trifluoromethylstyrene, p-dibromomethylstyrene, p-trifluoromethylstyrene, p-perfluorophenoxystyrene, p-bis(trifluoromethyl)aminostyrene and p-(1H-imidazolyloxy)styrene. However, the examples are not limited to the above-cited compounds.

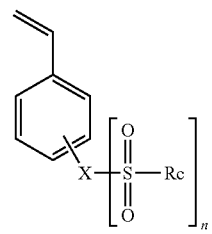

Formula (6)

(In Formula, Rc each independently represents an alkyl group containing an electron withdrawing group, an aryl group or a heteroaryl group containing an electron withdrawing group; X represents an atom which can be bonded, except for a carbon atom, or a single bond; and n represents an integer of not more than a value of an atomic valence of X minus 1.)

Examples of a compound represented by Formula (6) are: p-(methanesulfonyloxy)styrene, p-(trifluoromethanesulfonyloxy)styrene, p-tosylstyrene, p-(perfluoropropylsulfonyloxy)styrene, p-(perfluorobenzenesulfonyloxy)styrene and (4-vinylphenyl)bis(trifluoromethane sulfonyl)amide. However, the examples are not limited to the above-cited compounds.

Moreover, in the present invention, there can be used an alcohol compound such as ethylene glycol, glycerol, triethylene glycol, polyethylene glycol, polyvinyl alcohol, 4,4-methylenebisphenol, and further, there can be used an amino alcohol or an amino phenol having both an amino group and a hydroxyl group such as ethanolamine, aminobutyl phenol and 4-(4-aminobenzyl)phenol (ABP).

<<Macromonomer>>

In the present invention, one of the preferable embodiments is a compound having the aforesaid urea bond or thiourea bond which is produced from a macromonomer having a molecular weight of 400 to 10,000 as a raw material.

In the present invention, "a macromonomer" is a compound having the following structure: it has an isocyanate group, a group having an active hydrogen atom, or a polymerizable functional group such as a vinyl group at least at one portion of the molecular chain terminals; and it has two or more bonds selected from the group consisting of a urea bond (—NR$_1$CONR$_2$—), a thiourea bond (—NR$_3$CSNR$_4$—), a urethane bond (—OCOCR$_1$—), an amide bond (—CONR$_1$—), an ether bond (—O—), ester bond (—CO$_2$—) and a carbonate bond (—OCO$_2$—).

Moreover, in the present invention, R$_1$ in the urethane bond represents a hydrogen atom or an alkyl group having 1 to 10 carbon atoms (for example, a methyl group, an ethyl group, a propyl group, an isopropyl group, a tert-butyl group, a pentyl group, a hexyl group and a cyclohexyl group). Preferably, it is a hydrogen atom or an alkyl group having 5 carbon atoms or less, and more preferably, it is a hydrogen atom or a methyl group. Further, R$_1$ in the amide bond represents a hydrogen atom or an alkyl group having 1 to 10 carbon atoms (for example, a methyl group, an ethyl group, a propyl group, an isopropyl group, a tert-butyl group, a pentyl group, a hexyl group and a cyclohexyl group). Preferably, it is a hydrogen atom or an alkyl group having 5 carbon atoms or less, and more preferably, it is a hydrogen atom or a methyl group.

The macromonomer according to the present invention preferably contains a urea bond or a thiourea bond which exhibits a dipole moment. That is, since the macromonomer according to the present invention can be introduced a plurality of bonds or linking groups which have a dipole moment by allowing to condense successively the monomers which have a reactive group. As a results, controlling of the solubility or stiffness of the resin composition, which have been difficult to achieve, can be realized by selecting raw materials.

In addition, a urea bond is represented by Formula: —$NR_1CONR_2$— and a thiourea bond is represented by Formula: —$NR_3CSNR_4$—.

Here, $R_1$ and $R_2$, as well as $R_3$ and $R_4$ each independently represents a hydrogen atom or an alkyl group having 1 to 10 carbon atoms (for example, a methyl group, an ethyl group, a propyl group, an isopropyl group, a test-butyl group, a pentyl group, a hexyl group and a cyclohexyl group). Preferably, they are a hydrogen atom or an alkyl group having 5 carbon atoms or less, and more preferably, they are a hydrogen atom or a methyl group.

Although a urea bond or a thiourea bond may be formed using any means, it can be obtained by the reaction of an isocyanate with an amine, or by the reaction of an isothiocyanate with an amine. Or it may be obtained by a macromonomer which is prepared by a urea compound having a hydroxyl group or an amino group at a terminal position such as: 1,3-bis(2-aminoethyl)urea, 1,3-bis(2-hydroxyethyl)urea, 1,3-bis(2-hydroxypropyl)urea, 1,3-bis(2-hydroxymethyl) thiourea, 1,3-bis(2-hydroxyethyl)thiourea and 1,3-bis(2-hydroxypropyl)thiourea.

Although an isocyanate used as a raw material is not specifically limited as long as it is a polyisocyanate having at least two isocyanate groups in the molecule. An alkyl polyisocyanate or an aromatic polyisocyanate is preferable, and an alkyl diisocyanate or an aromatic diisocyanate is still more preferable. Moreover, it may be used together an unsymmetrical diisocyanate (for example, p-isocyanatobenzyl isocyanate) as a raw material.

An alkyl polyisocyanate is a compound in which all of a plurality of isocyanate groups exist through an alkyl chain. Examples thereof are: 1,3-bis(isocyanatomethyl)cyclohexane, isophorone diisocyanate, trimethylene diisocyanate, tetramethylene diisocyanate, pentamethylene diisocyanate, hexamethylene diisocyanate and 1,3-cyclopentane diisocyanate.

An aromatic polyisocyanate is a compound in which all of a plurality of isocyanate groups is directly bonded with an aromatic ring. Examples thereof are: 9H-fluorene-2,7-diisocyanate, 9H-fluorene-9-one-2,7-diisocyanate, 4,4'-diphenylmethane diisocyanate, 1,3-phenylene diisocyanate, trilene-2,4-diisocyanate, trilene-2,6-diisocyanate, 1,3-bis(isocyanatomethyl)cyclohexane, 2,2-bis(4-isocyanatophenyl)hexafluoropropane and 1,5-diisocyanatonaphthalene.

As an amine used for a raw material, a polyamine having two or more amino groups in the molecule is preferred, and a diamine is most preferred. Examples of a polyamine include: 2,7-diamino-9H-fluorene, 3,6-diaminoacridine, acriflavine, acridine yellow, 2,2-bis(4-aminophenyl)hexafluoropropane, 4,4'-diaminobenzophenone, bis(4-aminophenyl)sulfone, 4,4'-diaminodiphenyl ether, bis(4-aminophenyl)sulfide, 1,1-bis(4-aminophenyl)cyclohexane, 4,4'-diaminodiphenylmethane, 3,3'-diaminodiphenylmethane, 3,3'-diaminobenzophenone, 4,4'-diamino-3,3'-dimethyldiphenylmethane, 4-(phenyldiazenyl)benzene-1,3-diamine, 1,5-diaminonaphthalene, 1,3-phenylenediamine, 2,4-diaminotoluene, 2,6-diaminotoluene, 1,8-diaminonaphthalene, 1,3-diaminopropane, 1,3-diaminopentane, 2,2-dimethyl-1,3-propanediamine, 1,5-diaminopentane, 2-methyl-1,5-diaminopentane, 1,7-diaminoheptane, N,N-bis(3-aminopropyl)methylamine, 1,3-diamino-2-propanol, diethylene glycol bis(3-aminopropyl)ether, m-xylylenediamine, tetraethylenepentamine, 1,3-bis(aminomethyl)cyclohexane, benzoguanamine, 2,4-diamino-1,3,5-triazine, 2,4-diamino-6-methyl-1,3,5-triazine, 6-chloro-2,4-diaminopyrimidine and 2-chloro-4,6-diamino-1,3,5-triazine. These polyamines may be allowed to react with phosgene, triphosgene, or thiophosgene to prepare a polyisocyanate or a polyisothiocyanate (hereafter, they are called as polyiso(thio)cyanate). They can be used as a raw material for preparing a macromonomer. These polyamines may be used as a chain extending agent.

When a macromonomer is prepared, a highly ordered macromonomer can be prepared by using the difference of the reactivity between an amino group and a hydroxyl group. For this reason, it is preferable that a macromonomer has at least one urethane bond. A urethane bond can be obtained by the reaction of a hydroxyl group and an isocyanate group. Examples of a compound having a hydroxyl group are: a polyol, an amino alcohol, an amino phenol and an alkylamino phenol. Preferable compounds are a polyol and an amino alcohol, and more preferred compound is an amino alcohol.

A polyol is a compound having two or more hydroxyl groups in the molecule. A diol is preferably used. Examples of a polyol are: ethylene glycol, propylene glycol, 1,4-butanediol, 1,5-pentanediol, 1,6-hexanediol, neopentyl glycol, polyethylene glycol, polytetramethylene glycol, 1,4-cyclohexanedimethanol, pentaerythritol, 3-methyl-1,5-pentanediol, poly(ethylene adipate), poly(diethylene adipate), poly(propylene adipate), poly(tetramethylene adipate), poly(hexamethylene adipate) and poly(neopentylene adipate).

An amino alcohol is a compound having both an amino group and a hydroxyl group in the molecule. Examples of an amino alcohol are: aminoethanol, 3-amino-1-propanol, 2-(2-aminoethoxy)ethanol, 2-amino-1,3-propanediol, 2-amino-2-methyl-1,3-propanediol and 1,3-diamino-2-propanol. In addition, these compounds having a hydroxyl group may be used as a chain extending agent.

The macromonomer may contain an amide bond or a carbonate bond other than a urea bond, a thiourea bond, a urethane bond, an ester bond or an ether bond.

In addition, when comparing the material containing a urea bond with the material containing a thiourea bond, the thiourea structure is preferable from the viewpoint of large piezoelectricity and excellent in handling property by considering the magnitude of a dipole moment and the strength of a hydrogen bonding.

Although the macromonomer has a molecular weight of 400 to 10,000, it may have a molecular weight distribution since it will contains a dimer or a timer produced during the consecutive preparation steps. Here, the molecular weight designates a weight average molecular weight determined by a gel permuation chromatography (hereafter, it is called as "GPC"). The molecular weight is preferably 400 to 5,000, and more preferably it is 400 to 3,000. The molecular weight distribution is preferably 1.0 to 6.0, more preferably, it is 1.0 to 4.0, and still more preferably, it is 1.0 to 3M.

The measurements of the molecular weight and the molecular weight distribution can be done in accordance with the following method and conditions.

Solvent: 30 mM LiBr in N-methylpyrrolidone
Apparatus: HLC-8220 GPC (made by Tosoh Co., Ltd.)
Column: TSK-Gel Super AWM-H×2 (made by Tosoh Co., Ltd.)
Column temperature: 40° C.
Sample Concentration: 1.0 g/L
Injection amount: 40 µl
Flow rate: 0.5 ml/min Calibration curve: using a calibration curve prepared by 9 samples of Standard polystyrene (PS-1, made by Polymer Laboratories Co., Ltd.) having Mw of 580 to 2,560,000.

In the present invention, since a resin composition having a piezoelectric property can be produced by polymerizing a macromonomer, it is preferable that at least one of terminal groups of the macromonomer is an isocyanate group, a group having an active hydrogen atom, a vinyl group, an acryloyl group, or a meth acryloyl group. As a group which has an active hydrogen atom, although an amino group, a hydroxyl group, a carboxyl group, an imino group, or a thiol group is cited, a preferable group is an amino group, a hydroxyl group, or a carboxyl group, and more preferable group is an amino group or a hydroxyl group.

In order to increase the orientation property of the macromonomer or the prepared resin composition, it is preferable to polymerize together with a compound having a large dipole moment in the molecule such as a compound represented by the aforesaid Formulas (4) to (6).

In order to improve an orientation property of a macromonomer or a polymerized resin composition, it is preferable that a macromonomer contains at least one condensed aromatic cyclic structure as a partial structure of a macromonomer. Examples of a condensed aromatic cyclic structure include: a naphthalene structure, a quinoline structure, an anthracene structure, a phenanthrene structure, a pyrene structure, a triphenylene structure, a perylene structure, a fluoranthene structure, an indacene structure, an acenaphthylene structure, a fluorene structure, a fluorene-9-one structure, a carbazole structure, a tetraphenylene structure and a structure further condensed with these structures (for example, an acridine structure, a benzanthracene structure, a benzopyrene structure, a pentacene structure, a coronene structure and a chrysene structure.)

Examples of a preferable condensed aromatic cyclic structure are represented by Formulas (ACR1) to (ACR4) as described below.

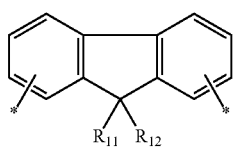

Formulas (ACR1)

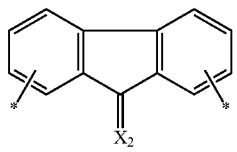

Formulas (ACR2)

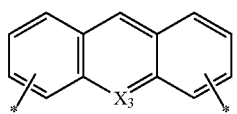

Formulas (ACR3)

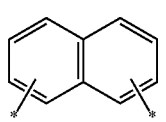

Formulas (ACR4)

In Formula (ACR1), $R_{11}$ and $R_{12}$ each independently represents a hydrogen atom, or a substituent. Examples of the substituent are: an alkyl group having 1 to 25 carbon atoms (for example, a methyl group, an ethyl group, a propyl group, an isopropyl group, and a tert-butyl group, a pentyl group, a hexyl group and a cyclohexyl group), a cycloalkyl group (for example, a cyclohexyl group and a cyclopentyl group), an aryl group (for example, a phenyl group), a heterocyclic group (for example, a pyridyl group, a thiazolyl group, an oxazolyl group, an imidazolyl group, a furyl group, a pyrrolyl group, a pyrazinyl group, a pyrimidinyl group, a pyridazinyl group, a selenazolyl group, a sulfolanyl group, a piperidinyl group, a pyrazolyl group and a tetrazolyl group), an alkoxy group (for example, a methoxy group, an ethoxy group, a propyloxy group, a pentyloxy group, a cyclopentyloxy group, a hexyloxy group and a cyclohexyloxy group), an aryloxy group (for example, a phenoxy group), an acyloxy group (for example, an acetyloxy group and a propionyloxy group), an alkoxycarbonyl group (for example, a methyloxycarbonyl group, an ethyloxycarbonyl group and a butyloxycarbonyl group), an aryloxycarbonyl groups (for example, a phenyloxycarbonyl group), a sulfonamide group (for example, a methanesulfonamide group, an ethanesulfonamide group, a butanesulfonamide group, a hexanesulfonamide group, a cyclohexanesulfonamide group and a benzenesulfonamide group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, a phenylaminocarbonyl group and 2-pyridylaminocarbonyl group), a carboxyl group and a hydroxyl group. Preferable groups are: a hydrogen atom, a hydroxyl group, a carboxyl group, an alkoxy group, an acyloxy group and an alkyl group. More preferable groups are: a hydrogen atom, an alkyl group, a hydroxyl group and an acyloxy group. Specifically preferable groups are a hydrogen atom and an alkyl group.

In addition, the asterisk (*) indicates the bonding position.

In Formulas (ACR2), $X_2$ represents an oxygen atom, N—$R_{23}$, or C—$R_{24}$. $R_{23}$ represents a hydrogen atom, a hydroxyl group, an alkoxy group, an alkyl group, or an amino group, preferably $R_{23}$ represents a hydroxyl group or an alkoxy group. $R_{24}$ represents an alkyl group, an aryl group, or a heterocyclic group. Preferably, $R_{24}$ represents an alkyl group or an aryl group, and more preferably, $R_{24}$ represents an alkyl group.

In addition, the asterisk (*) indicates the bonding position.

In Formulas (ACR3), $X_3$ represents a nitrogen atom, or $N^{(+)}$—$R_{33}$. $R_{33}$ represents an alkyl group or an aryl group. When $X_3$ represents $N^{(+)}$, it may contain a counter ion to neutralize the charge. As a counter ion, for example, Cl$^-$, Br$^-$, I$^-$ and $BF_4^-$ can be cited.

In addition, the asterisk (*) indicates the bonding position.

In Formulas (ACR4), the asterisk (*) indicates the bonding position.

These condensed aromatic cyclic structures may contain a substituent. Examples of the substituent are: an alkyl group having 1 to 25 carbon atoms (for example, a methyl group, an ethyl group, a propyl group, an isopropyl group, and a tert-butyl group, a pentyl group, a hexyl group and a cyclohexyl group), a halogenated alkyl group (for example, a trifluoromethyl group and a perfluorooctyl group), a cycloalkyl group (for example, a cyclohexyl group and a cyclopentyl group), an alkynyl group (for example, a propargyl group), a glycidyl group, an acrylate group, a methacrylate group, an aryl group (for example, a phenyl group), a heterocyclic group (for example, a pyridyl group, a thiazolyl group, an oxazolyl group, an imidazolyl group, a furyl group, a pyrrolyl group, a pyrazinyl group, a pyrimidinyl group, a pyridazinyl group, a selenazolyl group, a sulfolanyl group, a piperidinyl group, a pyrazolyl group and a tetrazolyl group), a halogen atom (for example, a chlorine atom, a bromine atom, iodine atoms and a fluorine atom), an alkoxy group (for example, a methoxy group, an ethoxy group, a propyloxy group, a pentyloxy group, a cyclopentyloxy group, a hexyloxy group and a cyclohexyloxy group), an aryloxy group (for example, a phenoxy group), an alkoxycarbonyl group (for example, a methyloxycarbonyl group, an ethyloxycarbonyl group and a butyloxycarbonyl group), an aryloxycarbonyl groups (for example, a phenyloxycarbonyl group), a sulfonamide group (for example, a methanesulfonamide group, an ethanesulfonamide group, a butanesulfonamide group, a hexanesulfonamide group, a cyclohexanesulfonamide group and a benzenesulfonamide group), a sulfamoyl group (for example, an aminosulfonyl group, amethylaminosulfonyl group, a dimethylaminosulfonyl group, a butylaminosulfonyl group, a hexylaminosulfonyl group, a cyclohexylaminosulfonyl group, a phenylaminosulfonyl group and 2-pyridyl amino sulfonyl group, etc.), a urethane group (for example, a methylureido group, an ethylureido group, a pentylureido group, a cyclohexylureido group, a phenylureido group and 2-pyridyl ureido group), an acyl group (for example, an acetyl group, an propionyl group, a butanoly group, a hexanoly group, a cyclohexanoly group, a benzoyl group and a pyridinoyl group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, a phenylaminocarbonyl group and 2-pyridylaminocarbonyl group), an amide group (for example, an acetamide group, a propionamide group, a butaneamide group, a hexanamide group and a benzamide group), a sulfonyl group (for example, a methylsulfonyl group, an ethylsulfonyl group, a butylsulfonyl group, a cyclohexylsulfonyl group, a phenylslufonyl group and 2-pyridyl sulfonyl group), an amino group (for example, an amino group, an ethylamino group, a dimethylamino group, a butylamino group, a cyclopentylamino group, an anilino group and 2-pyridyl amino group), a cyano group, a carboxyl group and a hydroxyl group. In addition, these groups may be further substituted with these groups. Moreover, when there are two or more substituents, they may be the same or different with each other, and they may be jointed with each other to form a condensed cyclic structure. Preferable groups are: a hydrogen atom, a halogen atom, an amide group, an alkyl group and an aryl group. More preferable groups are: a hydrogen atom, a halogen atom, an amide group and an alkyl group. Specifically preferable groups are a hydrogen atom, a halogen atom and an alkyl group.

Examples of a preferable condensed aromatic cyclic structure are shown below, however, the present invention is not limited to them.

Examples of a Condensed Aromatic Cyclic Structure

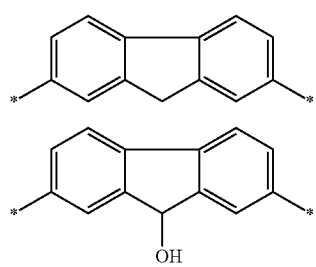

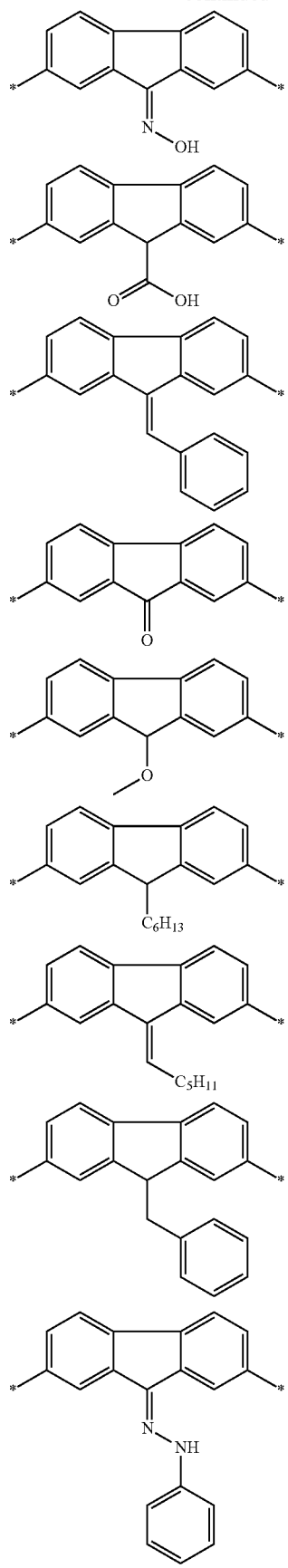

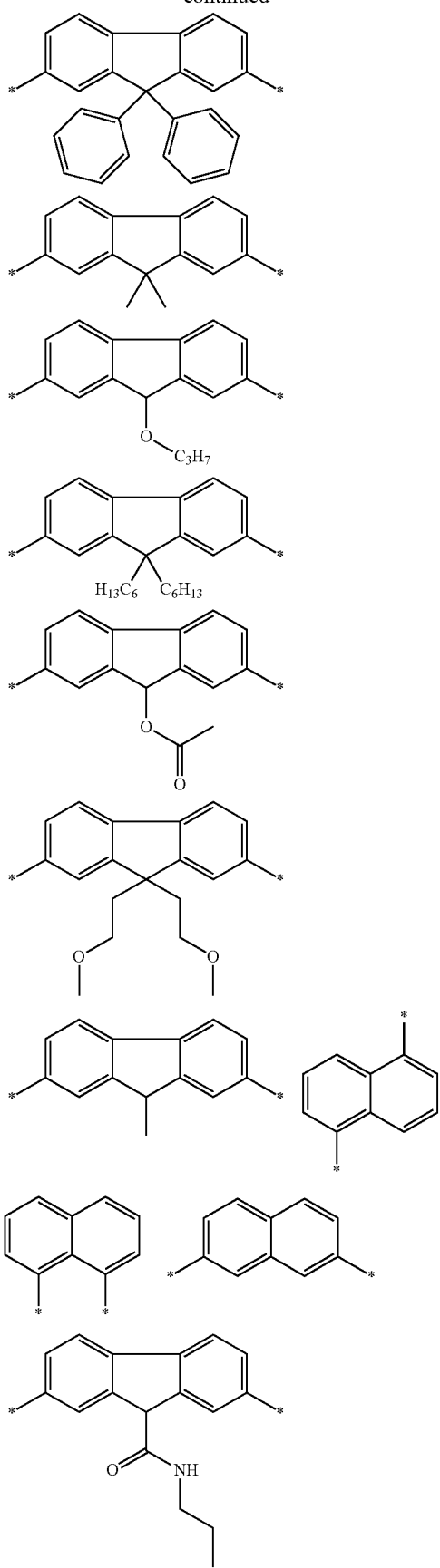
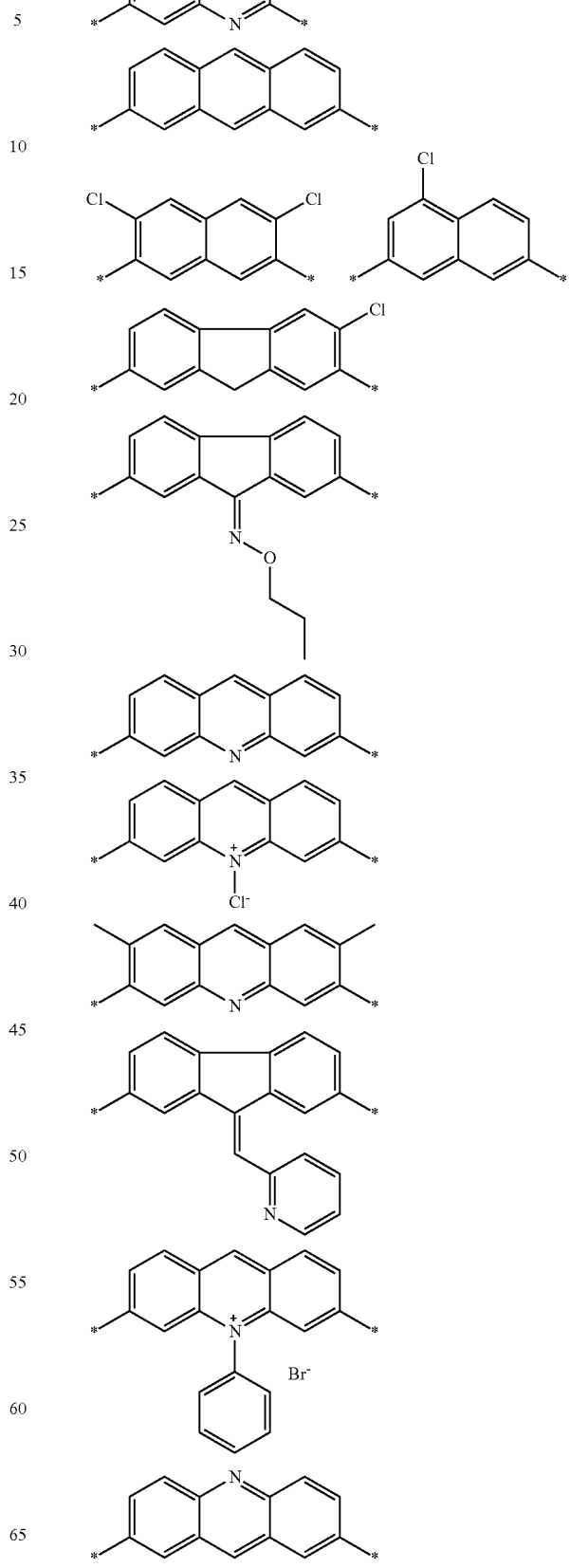

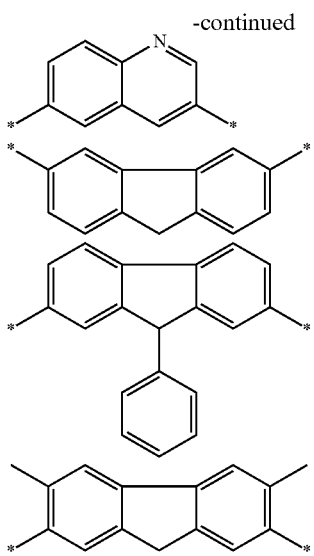

<<Synthesis of Macromonomer>>

A macromonomer can be synthesized by a method in which an active hydrogen-containing compound is allowed to serve as a starting material and then polyiso(thio)cyanate and the active hydrogen-containing compound are alternately condensed; or a method in which polyiso(thio)cyanate is allowed to serve as a starting material and then an active hydrogen-containing compound and the polyiso(thio)cyanate are alternately condensed.

As the active hydrogen-containing compound, the above-cited urea compounds substituted with an alkyl group having a hydroxyl group or an amino group at a terminal, polyamines, polyols, aminoalcohols, aminophenols, and alkylaminophenols are cited. As the starting material, urea compounds substituted with an alkyl group having a hydroxyl group or an amino group at a terminal or polyamines are preferable. Of these, polyamines having an aromatic condensed ring structure are more preferable. In the case of use in an alternate condensation process, aminoalcohols or polyols are preferable.

In the case of use of polyiso(thio)cyanate as a starting material, as the starting material, polyiso(thio)cyanate having an aromatic condensed ring structure is preferable. Via condensation with an active hydrogen-containing compound, a compound having active hydrogen at a terminal may be synthesized, or a diamine may be formed using the method described in JP-A No. 5-115841.

Further, a macromonomer having active hydrogen at a terminal is allowed to react with 3-chloro-1-butene, allyl chloride, acryloyl chloride, or methacryloyl chloride, whereby a macromonomer having a vinyl group, an acryloyl group, or a methacryloyl group at a terminal can be synthesized.

In reaction of polyiso(thio)cyanate with an active hydrogen-containing compound, when at least one terminal is allowed to be an isocyanate group, the used amount of the polyiso(thio)cyanate is preferably 1-10-fold mol based on the active hydrogen-containing compound, more preferably 1-5-fold mol, still more preferably 1-3-fold mol.

In reaction of polyiso(thio)cyanate with an active hydrogen-containing compound, when at least one terminal is allowed to be active hydrogen, the used amount of the active hydrogen-containing compound is preferably 1-10-fold mol based on the polyiso(thio)cyanate, more preferably 1-5-fold mol, still more preferably 1-3-fold mol.

Condensation reaction temperature is preferably as low as possible, being −40-60° C., preferably −20-30° C., more preferably −10-10° C. Further, the reaction temperature may be kept at a constant temperature from the reaction initiation to the termination. It is possible to employ a low temperate initially and thereafter to raise the temperature.

As a solvent used in the reaction, a highly-polar solvent needs to be used, since the targeted resin composition has high polarity and polymerization is required to proceed efficiently. A highly-polar aprotic solvent such as DMF (N,N-dimethylformamide), DMAc (N,N-dimethylacetamide), DMSO(dimethyl sulfoxide), or NMP (N-methylpyrrolidone) is preferably selected. However, if a reactive substance and a targeted substance are well dissolved, there may be used solvents including an aliphatic hydrocarbon such as cyclohexane, pentane, or hexane; an aromatic hydrocarbon such as benzene, toluene, or chlorobenzene; an ether such as THF (tetrahydrofuran), diethyl ether, or ethylene glycol diethyl ether; a ketone such as acetone, methyl ethyl ketone, or 4-methyl-2-pentanone; or an ester such as methyl propionate, ethyl acetate, or butyl acetate. These solvents may be used as a mixture.

To efficiently accelerate urethane-bond formation, usable is a well-known urethane-bond formation catalyst including a tertiary alkyl amine such as N,N,N',N'-tetramethyl-1,3-butanediamine, triethylamine, or tributylamine; a condensed ring amine such as 1,4-diazabicyclo[2.2.2]octane or 1,8-diazabicyclo[5.4.0]unde-7-ene; or an alkyl tin such as DBTL, tetrabutyltin, or tributyltin acetate.

In view of efficient reaction and reaction procedures, the used amount of such a catalyst is preferably 0.1-30 mol % based on a monomer substance.

A macromonomer may be isolated at each condensation process or synthesized in one pot, being, however, preferably isolated and purified on formation of a compound having active hydrogen at a terminal.

For purification of a macromonomer, any appropriate method may be used. However, purification via reprecipitation is preferable. The reprecipitation method is not specifically limited. But, a method is preferable in which a macromonomer is dissolved in a good solvent and then the resulting solution is dripped into a poor solvent for precipitation.

The "good solvent" referred to herein may be any solvent as long as the solvent dissolves such a macromonomer. A polar solvent is preferable. A highly-polar aprotic solvent such as DMF (N,N-dimethylformamide), DMAc (N,N-dimethylacetamide), DMSO(dimethyl sulfoxide), or NMP (N-methylpyrrolidone) can specifically be cited.

Further, the "poor solvent" may be any solvent unless the solvent dissolves the macromonomer. There can be cited an aliphatic hydrocarbon such as cyclohexane, pentane, or hexane; an aromatic hydrocarbon such as benzene, toluene, or chlorobenzene; an ether such as diethyl ether or ethylene glycol diethyl ether; an ester such as methyl propionate, ethyl acetate, or butyl acetate; and an alcohol such as methanol, ethanol, or propanol.

Specific examples of the macromonomer will now be listed that by no means limit the scope of the present invention.

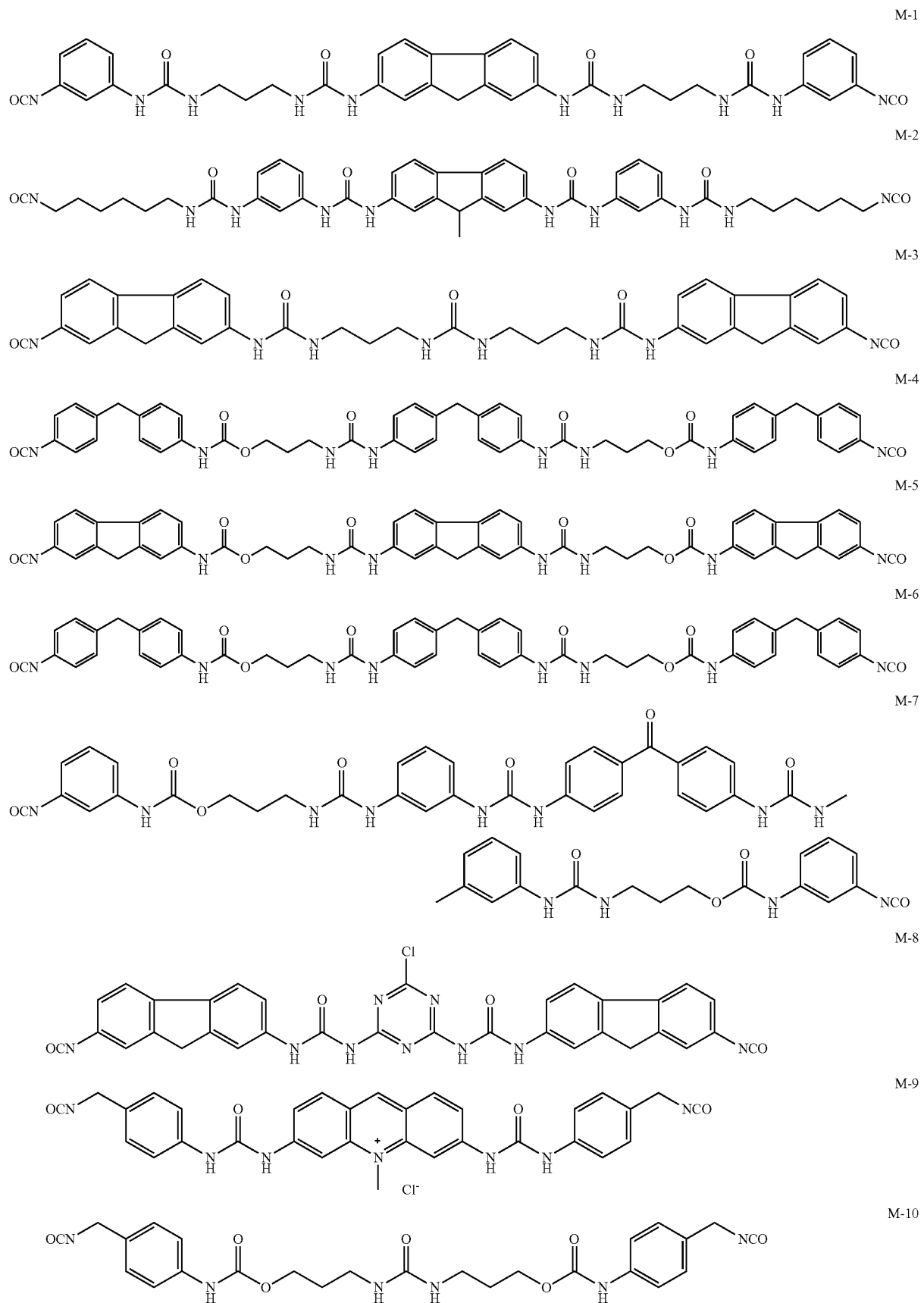

-continued
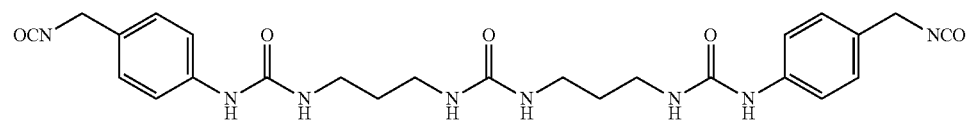
M-11
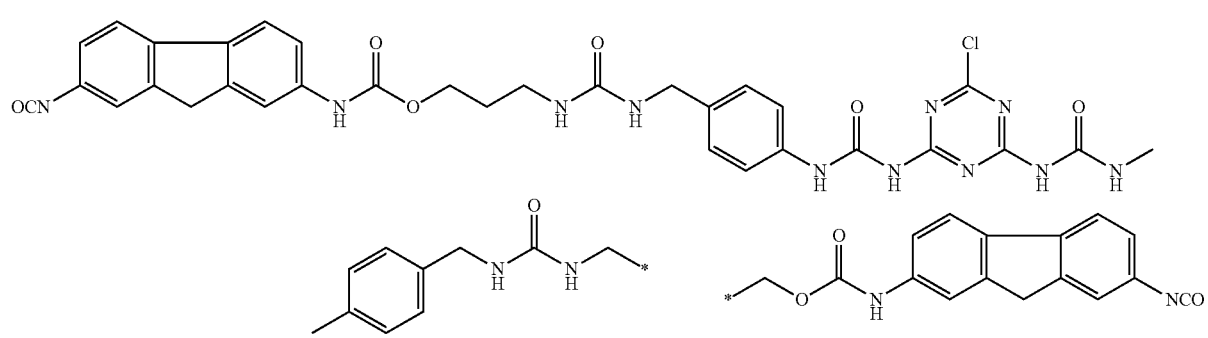
M-12
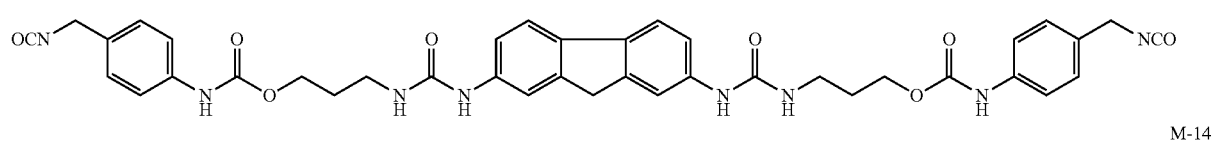
M-13
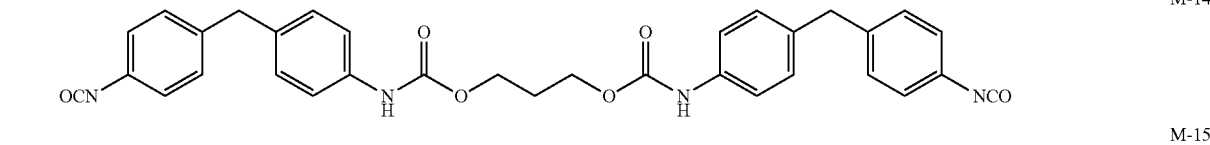
M-14
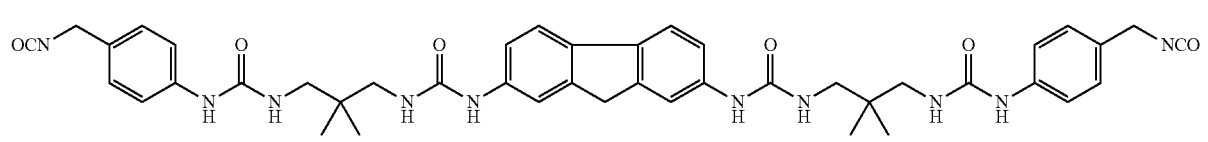
M-15
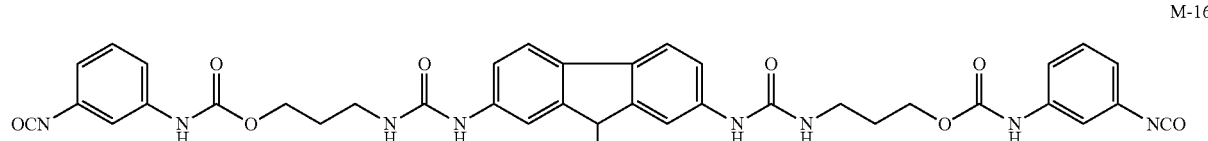
M-16
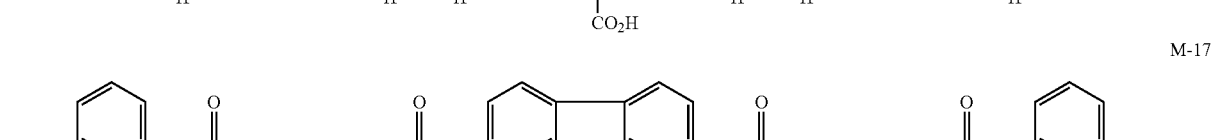
M-17
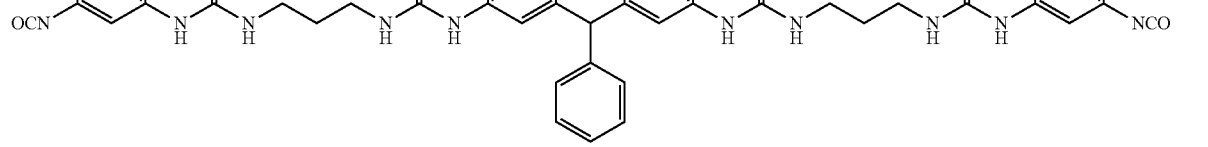
M-18
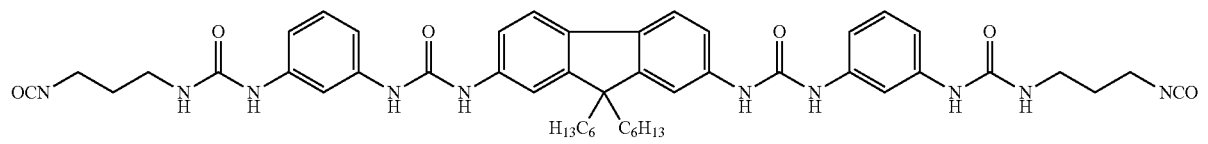
M-19
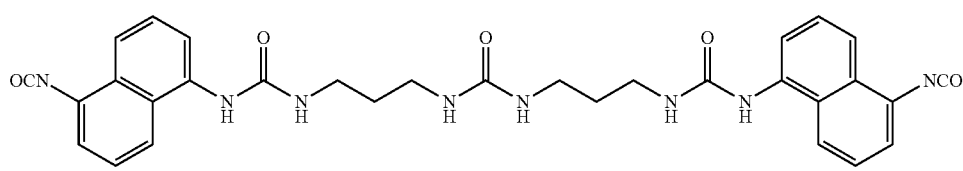

M-20
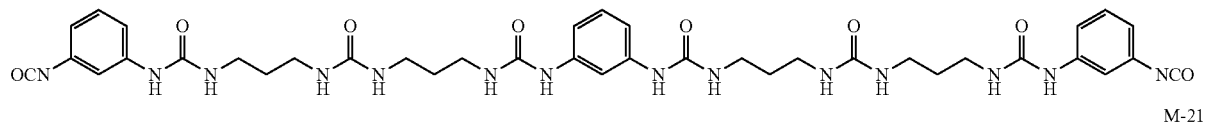
M-21
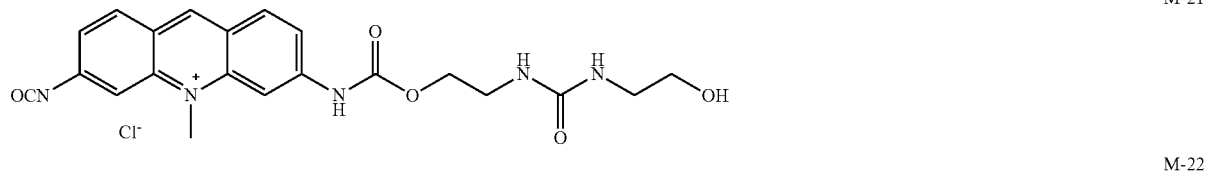
M-22
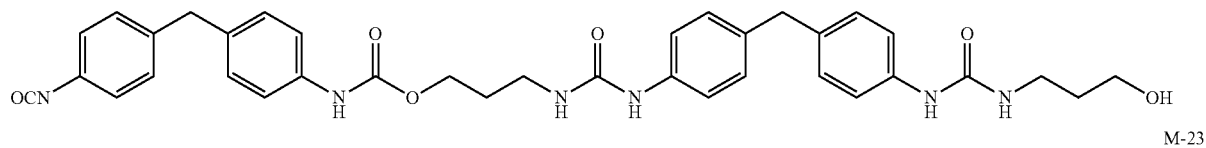
M-23
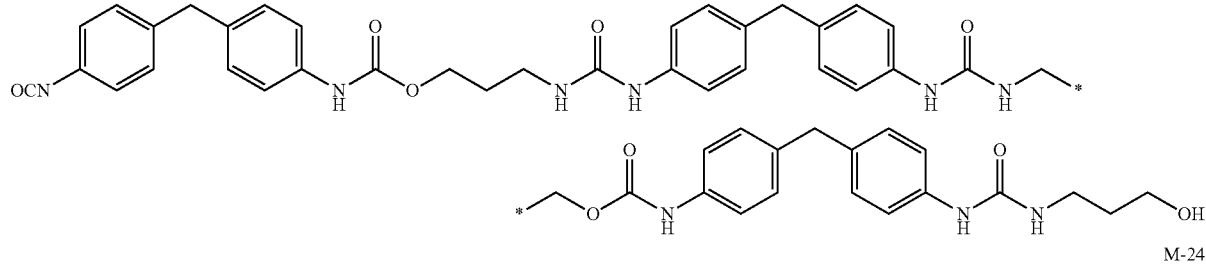
M-24
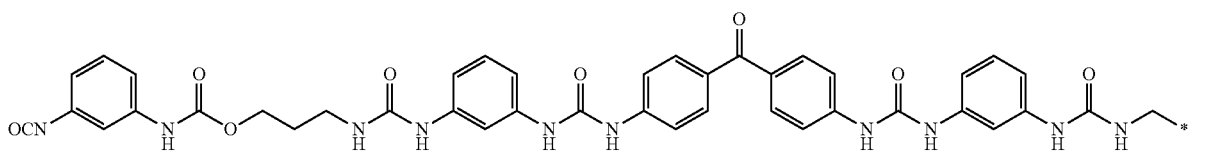
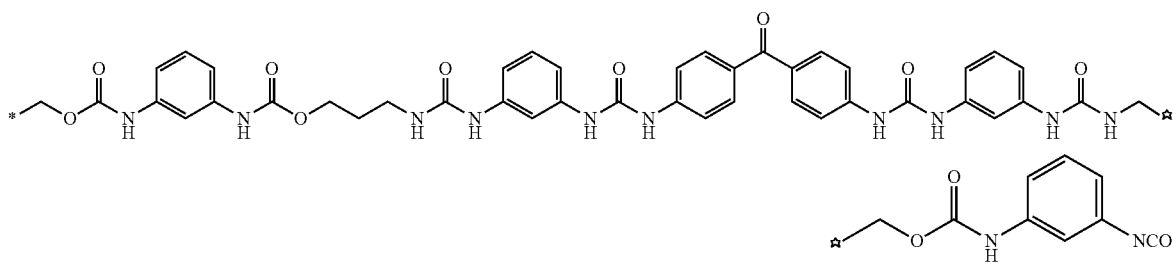
M-25
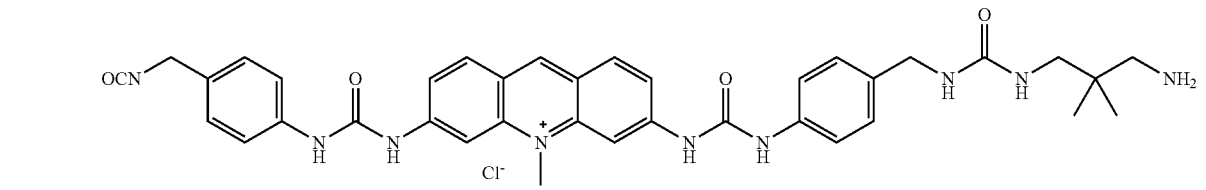
M-26
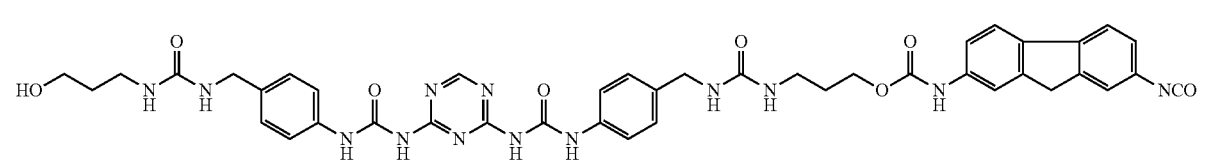

-continued
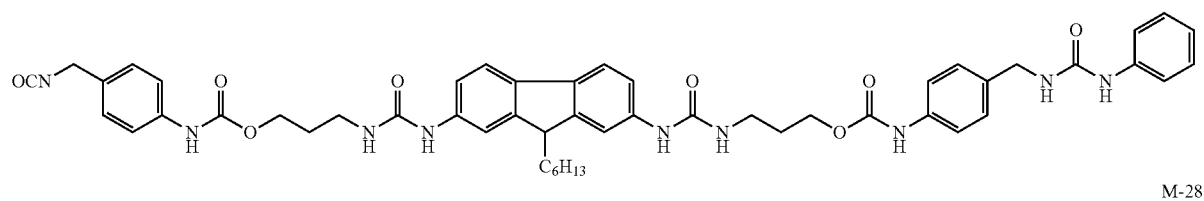
M-27
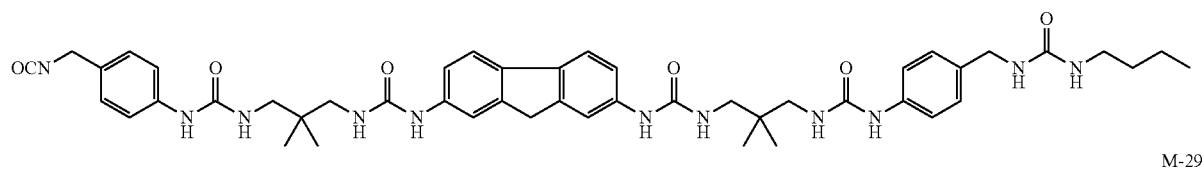
M-28
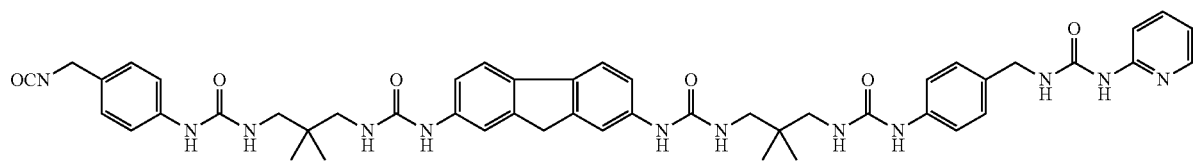
M-29
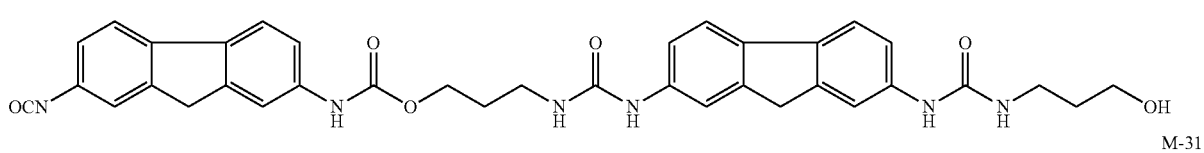
M-30
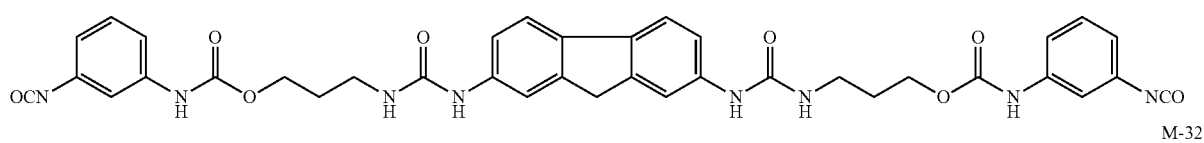
M-31
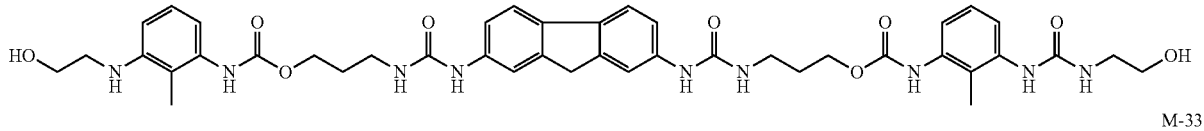
M-32
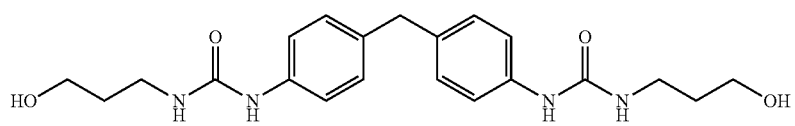
M-33
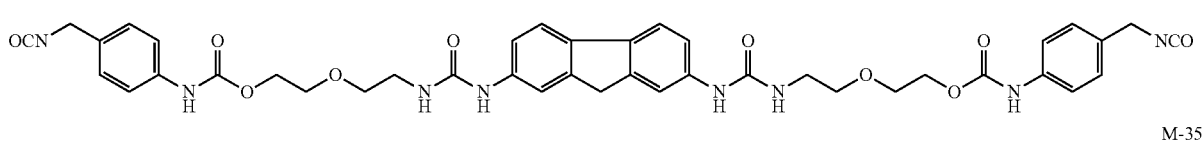
M-34
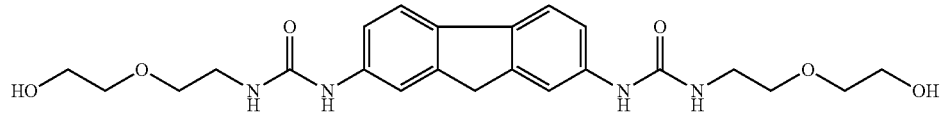
M-35
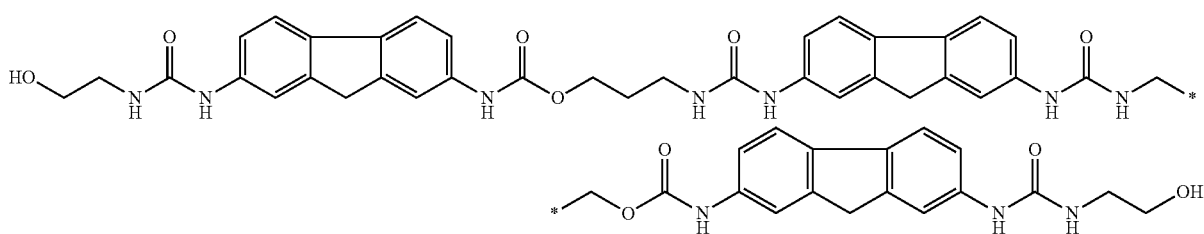
M-36

M-37
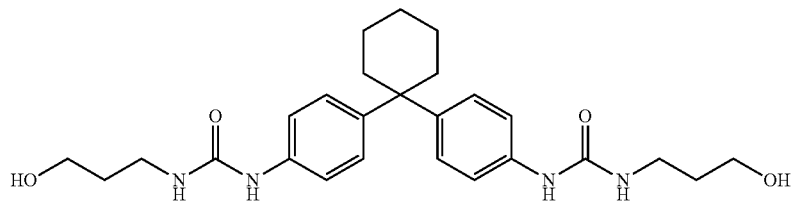
M-38
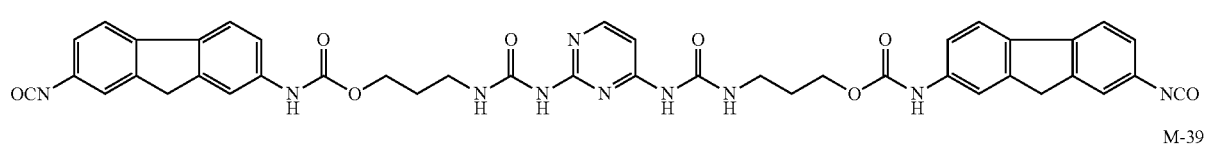
M-39
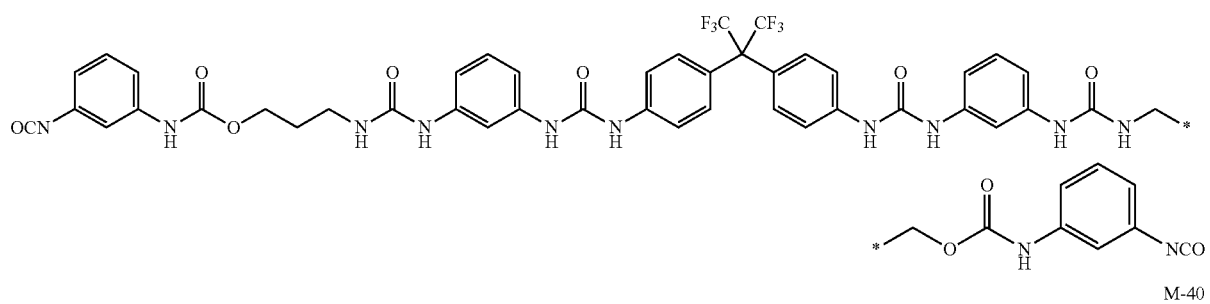
M-40
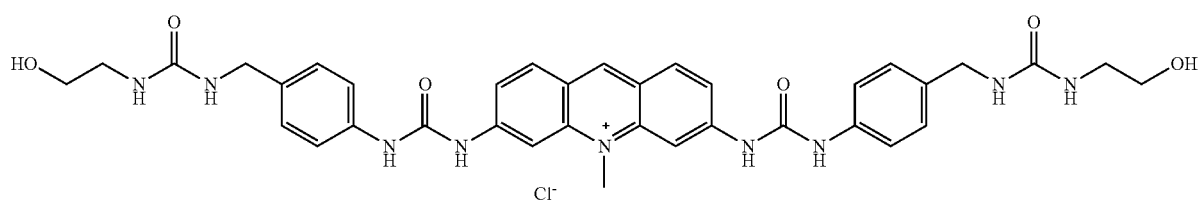
M-41
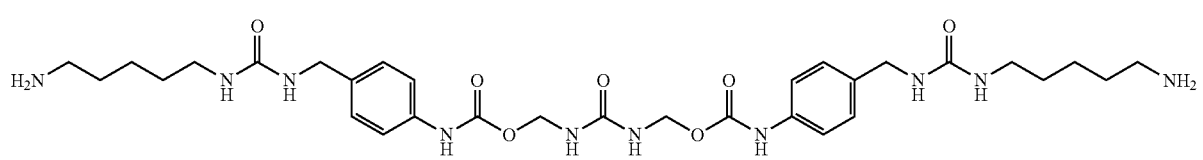
M-42
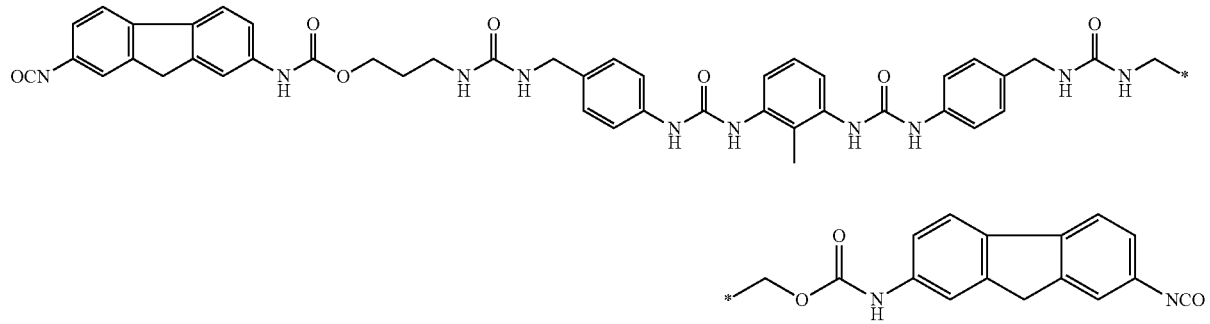
M-43
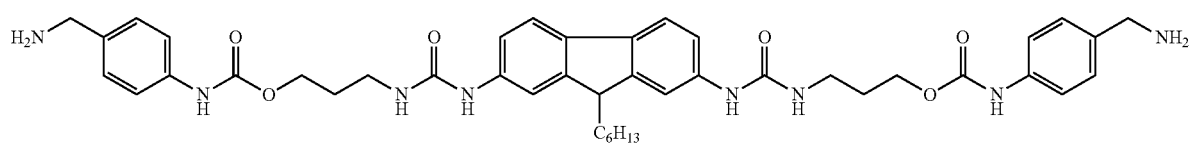

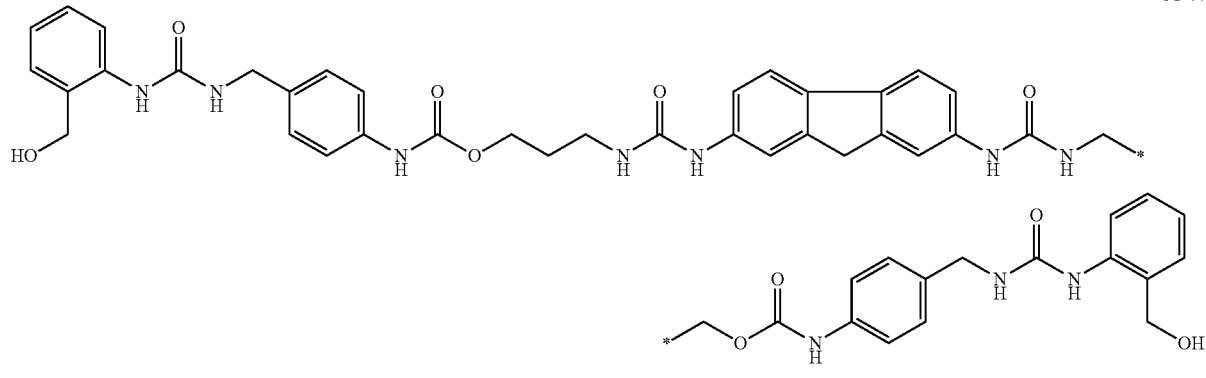
M-44
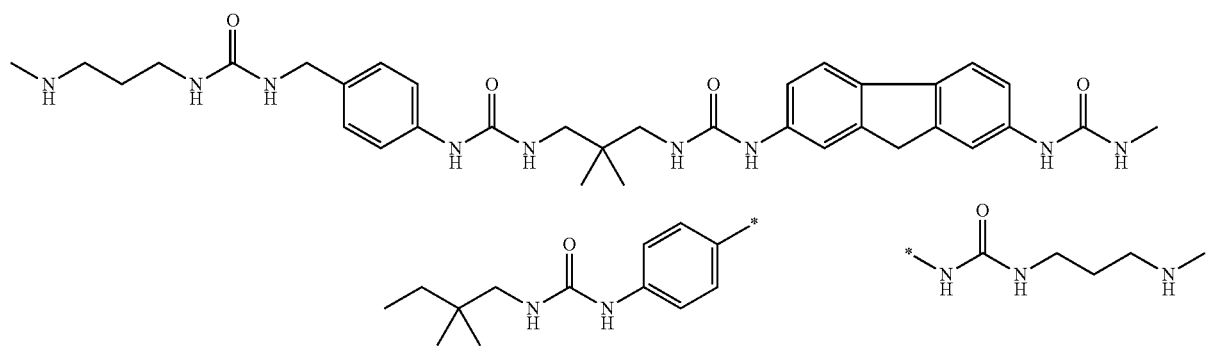
M-45
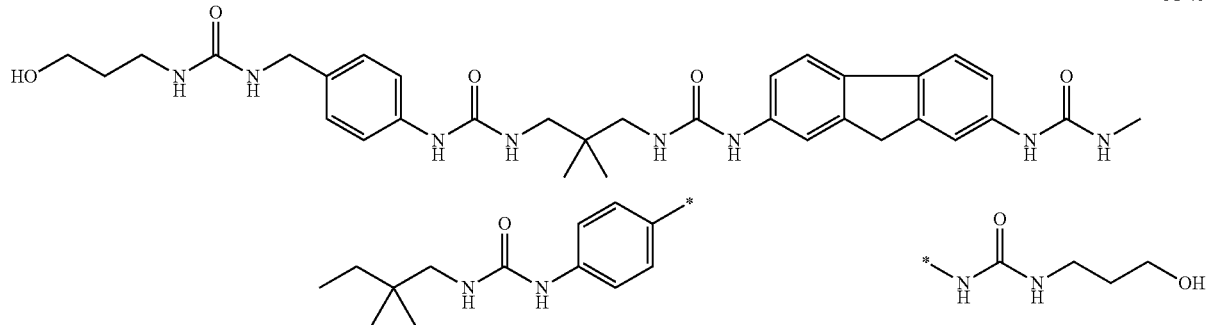
M-46
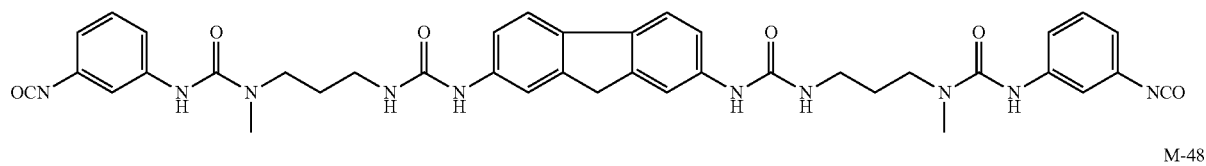
M-47
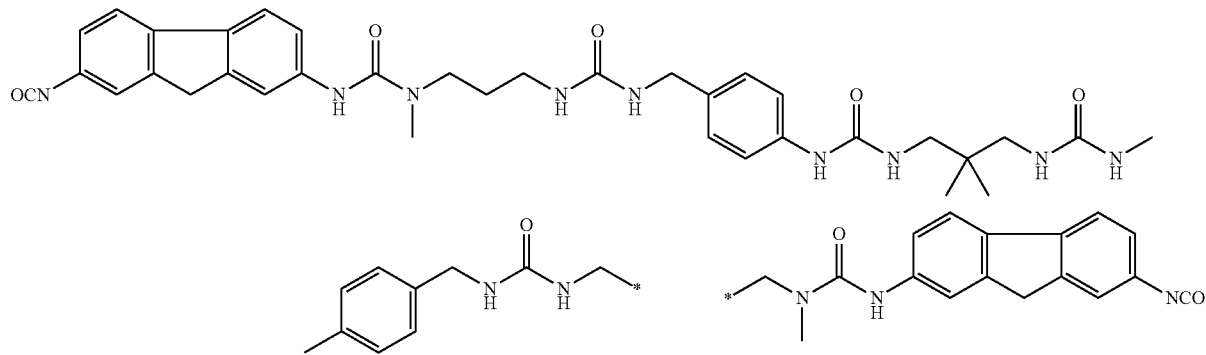
M-48

-continued
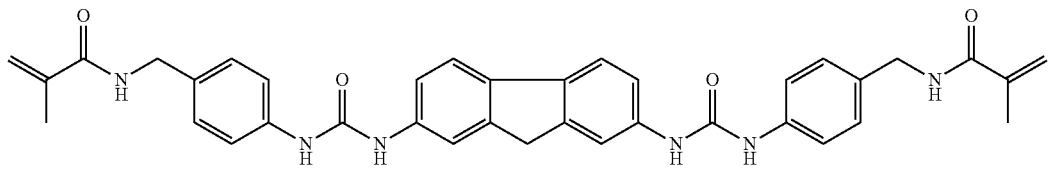
M-49
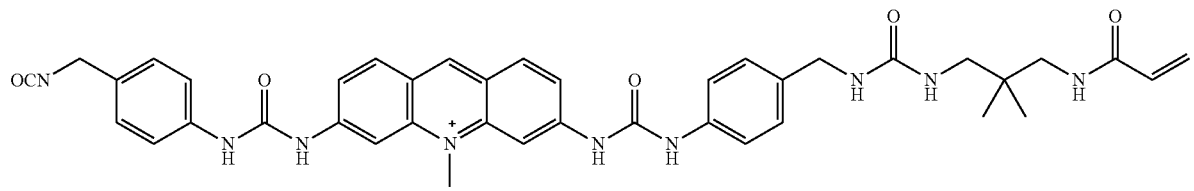
M-50
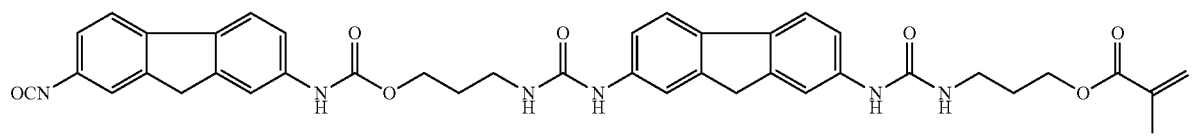
M-51
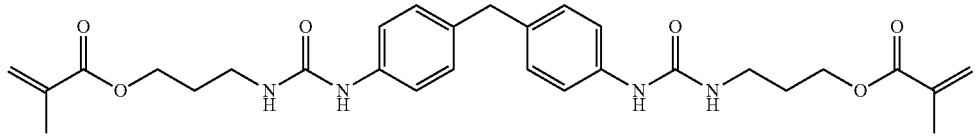
M-52
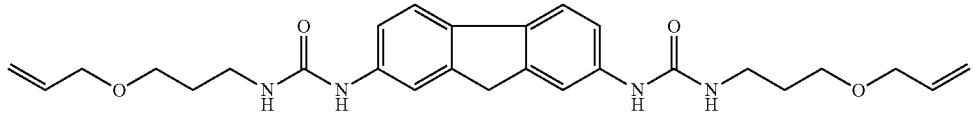
M-53
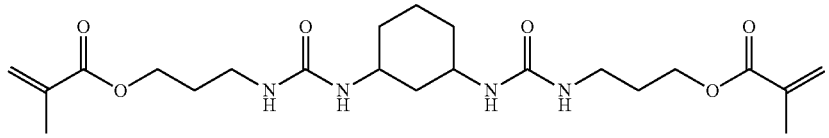
M-54
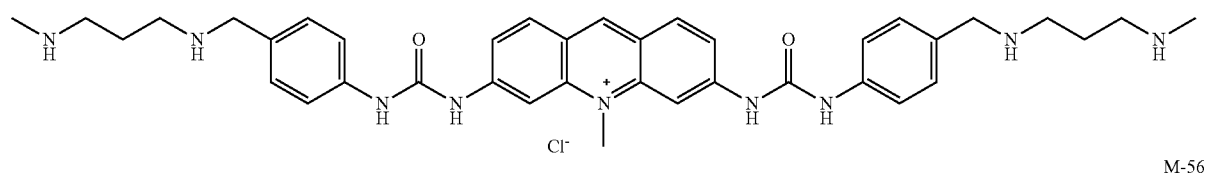
M-55
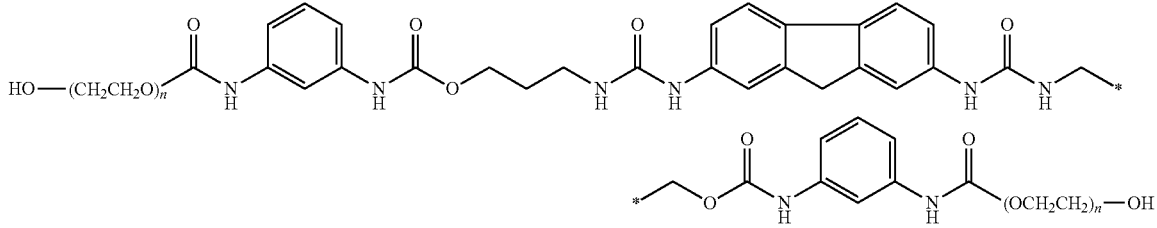
M-56
n = 1~10
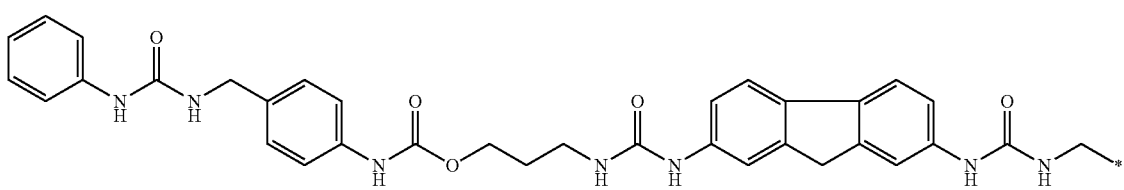
M-57

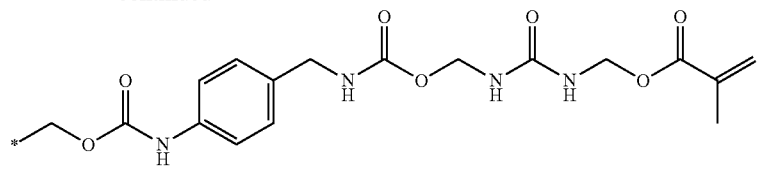
M-58
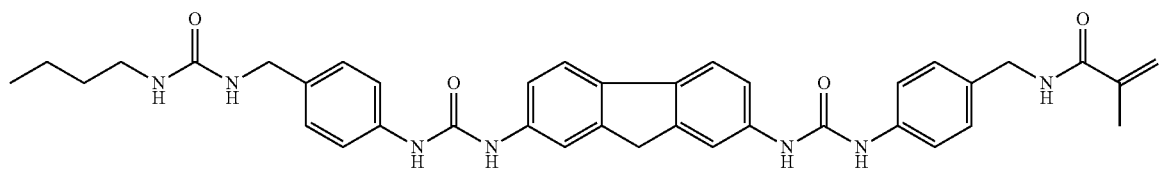
M-59
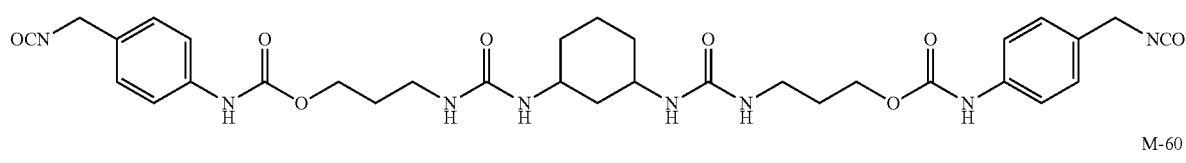
M-60
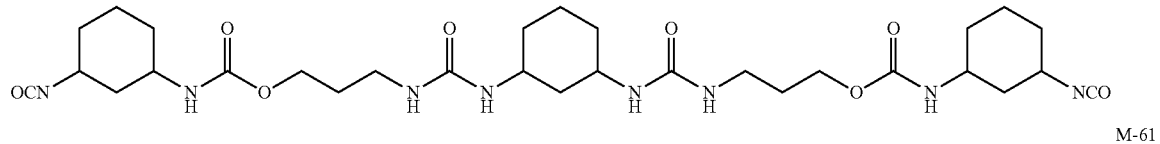
M-61
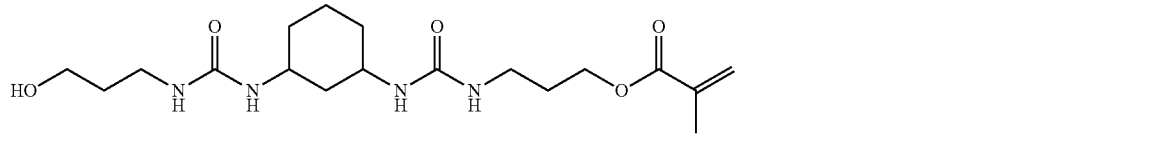
M-62
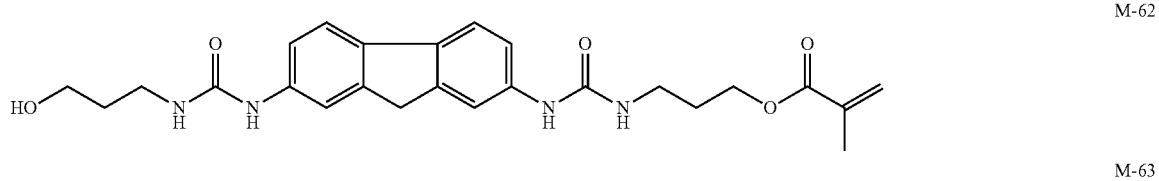
M-63
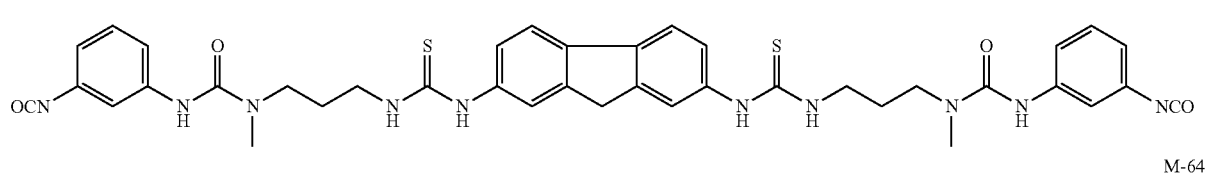
M-64
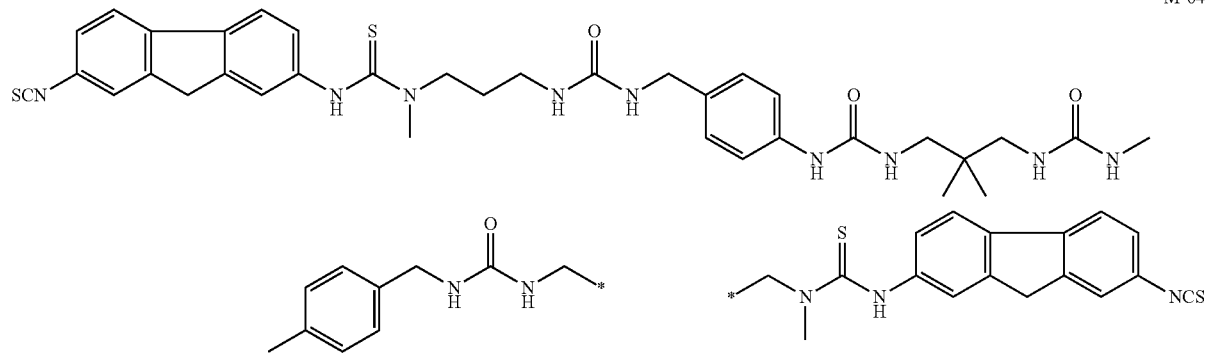
M-65
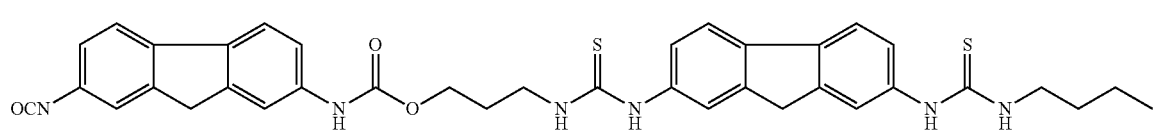

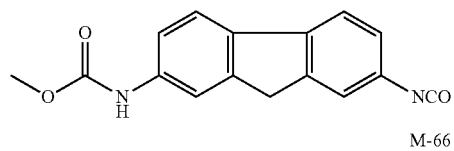
M-66
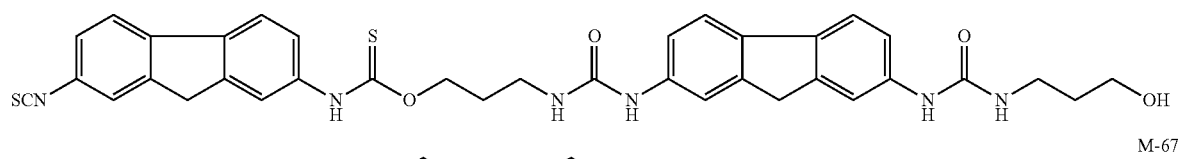
M-67
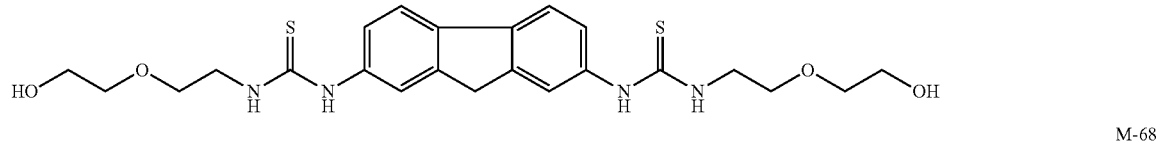
M-68
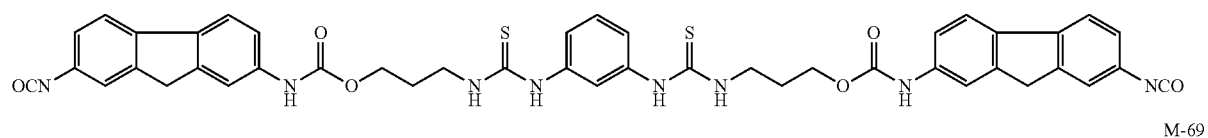
M-69
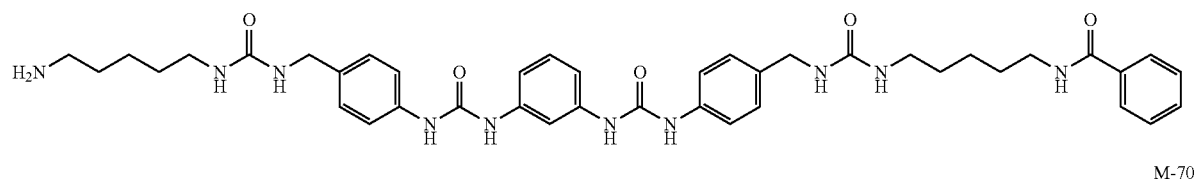
M-70
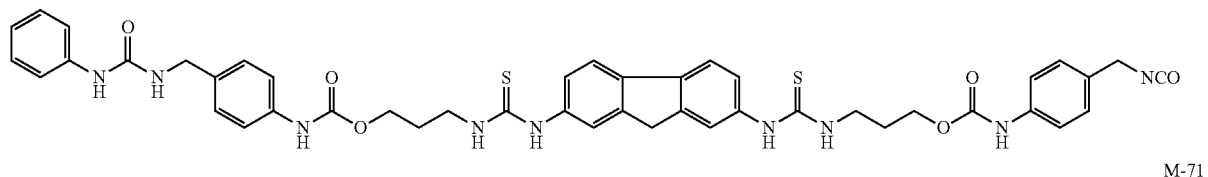
M-71
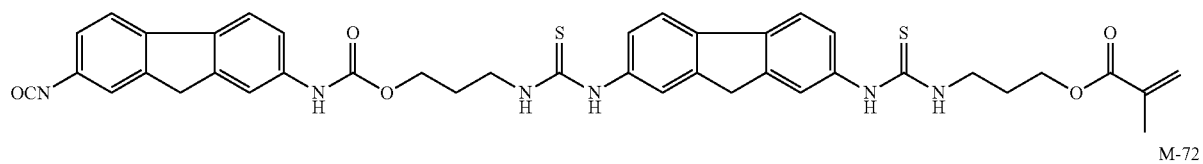
M-72
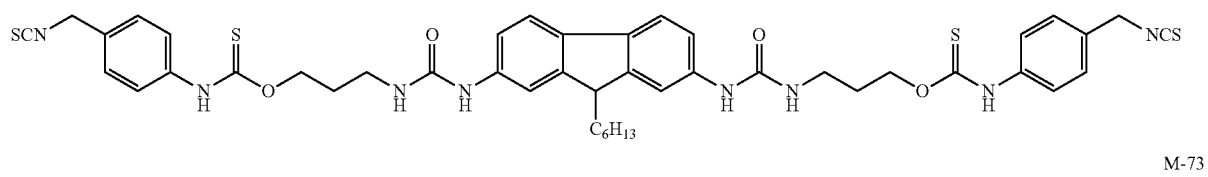
M-73
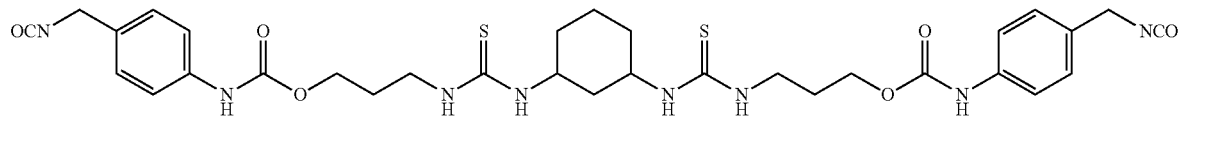
M-74
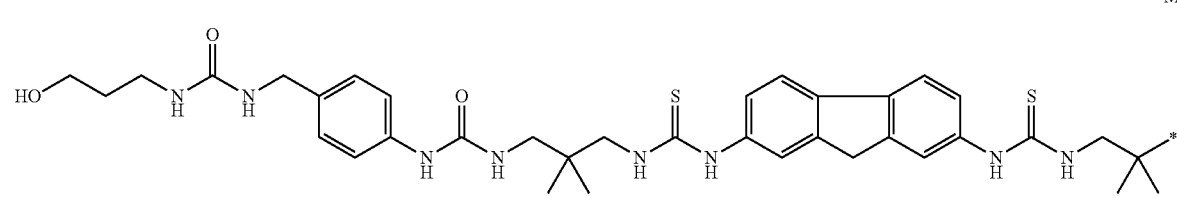

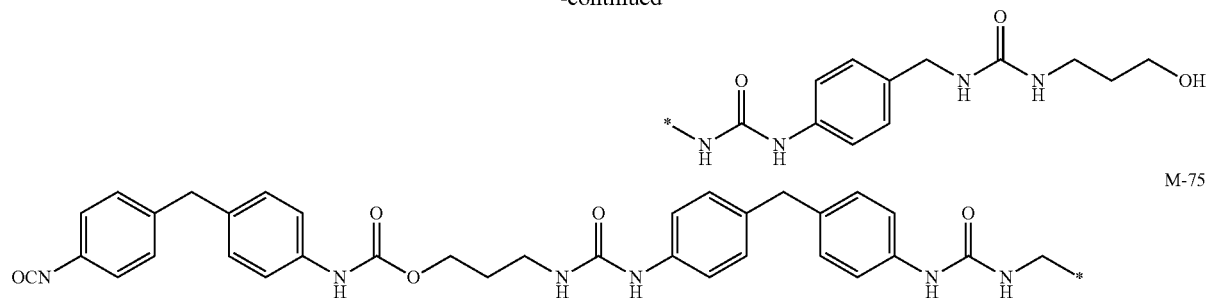
M-75
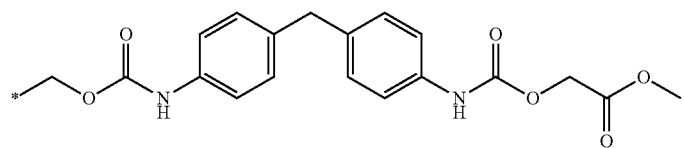
M-76
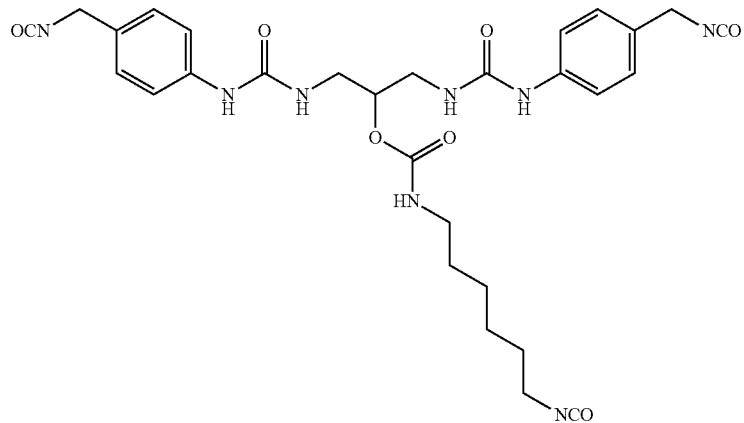
M-77
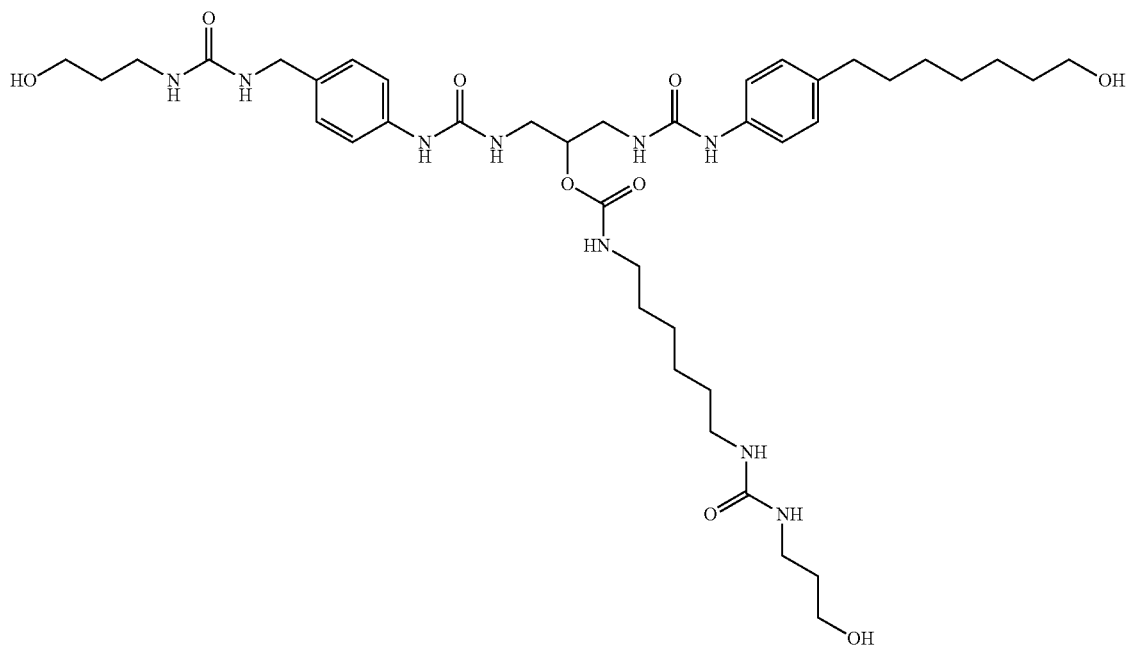

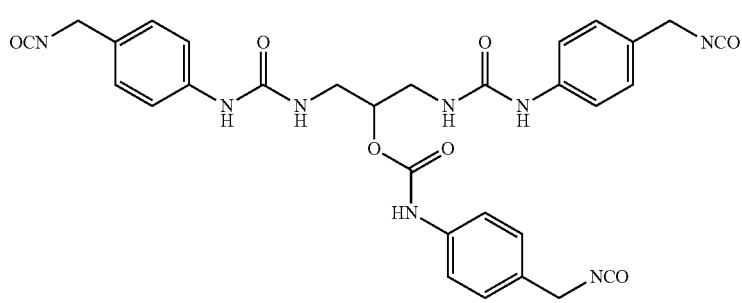

M-78

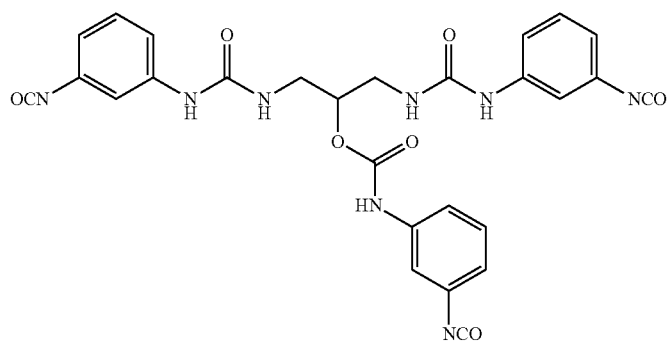

M-79

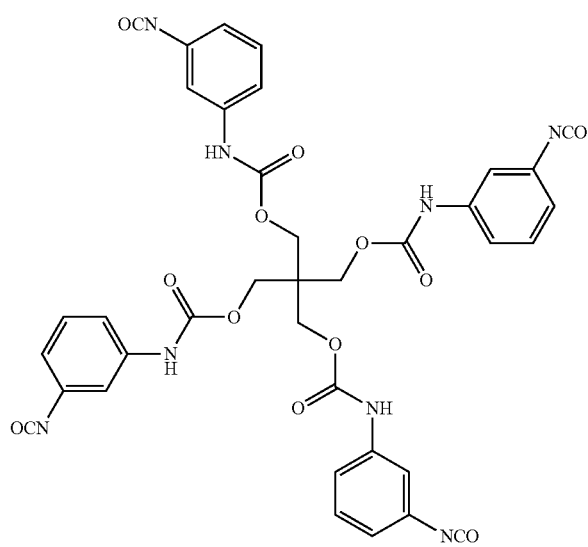

M-80

SYNTHESIS EXAMPLES OF MACROMONOMER

Synthesis Example 1

Synthesis of Macromonomer (M-8)

Under nitrogen atmosphere, 85.27 g of 9H-fluoren-2,7-diisocyanate was dissolved in 850 ml of THF, and therein, 5.0 g of 2-chloro-4,6-diamino-1,3,5-triazine having been dissolved in 50 ml of THF was slowly dripped at 0° C. After the termination of dripping, 1-hour stirring was conducted at 0° C., followed by 2-hour stirring at room temperature. The solvent in the reaction solution was concentrated under reduced pressure to distil away ⅔ thereof. Thereafter, reprecipitation was carried out using an ethyl acetate-heptane mixed solvent and the supernatant solution was removed by decantation, followed by reduced-pressure drying to obtain 20 g of a macromonomer (M-8), which was verified as the targeted substance using 1H-NMR.

Synthesis Example 2

Synthesis of Macromonomer (M-15)

Forty g of diethylamine was mixed with 50 ml of THF and 20 g of 9H-fluoren-2,7-diisocyanate having been dissolved in 50 ml of THF was dripped at room temperature. After the termination of dripping, 1-hour stirring was carried out at room temperature and then precipitates were filtered and washed with THF.

Subsequently, 30 g of the thus-obtained compound and 180 g of 2,2-dimethyl-1,3-propanediamine were mixed together and the resulting mixture was heated at 120° C. The distillate was removed, and then when no distillate was generated, reduced-pressure distillation was carried out under reduced pressure until no distillate was produced. The obtained residue was washed with THF and well dried to obtain 1,1'-(9H-fluoren-2,7-diyl)bis(3-(3-amino-2,2-dimethylpropyl)urea)).

Under nitrogen atmosphere, 7 g of p-isocyanatobenzyl isocyanate was dissolved in 70 ml of dimethyl sulfoxide and then the reaction solution was cooled to 0° C. Three g of 1,1'-(9H-fluoren-2,7-diyl)bis(3-(3-amino-2,2-dimethylpropyl)urea)) having been dissolved in 30 ml of dimethyl sulfoxide was slowly dripped. After the termination of dripping, 1-hour stirring was carried out at 0° C. The temperature was gradually raised and reaction was performed at room temperature for 1 hour, followed by reprecipitation with ethyl acetate. The supernatant solution was removed by decantation, followed by reduced-pressure drying to obtain 6.5 g of a macromonomer (M-15). Via GPC determination, the weight average molecular weight thereof was determined to be 810 and the molecular weight distribution was 1.6.

Synthesis Example 3

Synthesis of Macromonomer (M-31)

Under nitrogen atmosphere, 5.0 g of 9H-fluoren-2,7-diisocyanate was dissolved in 50 ml of THF, and therein, 3.2 g of 3-aminopropanol having been dissolved in 30 ml of THF was slowly dripped at 0° C. After the termination of dripping, 1-hour stirring was carried out at 0° C. to obtain a solution (A).

Dissolution of 13.0 g of 1,3-phenylenediisocyanate in 65 ml of THF was carried out. While the reaction solution was heated to 70° C., the solution (A) was dripped. After the termination of dripping, 5-hour stirring was carried out at 70° C. and then the solvent amount of the reaction solution was concentrated to ⅔ under reduced pressure. An ethyl acetate-heptane mixed solution was added to the residue and the resulting mixture was stirred. The supernatant solution was removed by decantation, followed by reduced-pressure drying to obtain 12.5 g of a macromonomer (M-31). Via GPC determination, the weight average molecular weight thereof was determined to be 750 and the molecular weight distribution was 2.0.

Synthesis Example 4

Synthesis of Macromonomer (M-35)

Under nitrogen atmosphere, 5.0 g of 9H-fluoren-2,7-diisocyanate was dissolved in 50 ml of THF, and therein, 10.0 g of 2-(2-aminoethoxy)ethanol having been dissolved in 30 ml of THF was slowly dripped at room temperature. After the termination of dripping, 3-hour stirring was carried out at room temperature. The residue was concentrated, followed by reprecipitation to obtain 2.9 g of a macromonomer (M-35), which was verified as the targeted substance using 1H-NMR.

<<Solvent>>

As a solvent usable during polymerization in the present invention, a solvent which is commonly used in polymer material synthesis can be used, including tetrahydrofuran, acetone, methyl ethyl ketone, ethyl acetate, methylene chloride, chloroform, toluene, and hexane with no limitation.

(Production Method of an Organic Piezoelectric Material)

The organic piezoelectric material of the present invention can be produced using any of the various well-known methods in the technological field. Investigations conducted by the present inventors made it clear that it was preferable, from the viewpoint of adhesion properties, to cast a layer containing particles according to the present invention so that the layer was brought into direct contact to a casting support. A method employing such casting will now be described.

(Production Process)

A production method of the organic piezoelectric material of the present invention will now be described with reference to the process chart shown in FIG. 1.

FIG. 1 is a process chart showing one example of a production apparatus for the organic piezoelectric material of the present invention. An organic piezoelectric material liquid 1a has been poured into the organic piezoelectric liquid tank 1 to prepare such an organic piezoelectric material liquid and also a fine particle added liquid 2a has been poured into the fine particle added liquid tank 2 The organic piezoelectric material liquid 1a is sent to the in-line mixers 5a and 5b by the pumps 4b and 4c. The fine particle added liquid 2a is sent to the in-line mixer 5a by the pump 4a. Using the in-line mixer 5a, the organic piezoelectric material liquid 1a and the fine particle added liquid 2a are well mixed to be sent to the slit of the slit die 6.

Similarly, using the in-line mixer 5b, the organic piezoelectric material liquid 1a and an additive liquid 3a are well mixed to be sent to the slit of the slit die 6. The upper and lower surface layers are constituted of a mixed liquid of the organic dielectric material liquid 1a and the fine particle added liquid 2a flowing from the slit die 6 and the middle layer is co-cast from the casting opening in the state of a mixed liquid of the organic piezoelectric material liquid 1a and the additive liquid 3a. Then, casting is carried out from the drum 7 onto the casting belt 8 which continuously moves. An organic piezoelectric material liquid layer containing the thus-cast 3 layers is dried and thereafter peeled from the casting belt by the roller 9 as an organic piezoelectric material laminated film 10.

Herein, in production of such an organic piezoelectric material, 3 layers may be "co-cast" as described above, or casting of a single layer may be employable using only the in-line mixer 5a into which particles are added.

A co-casting method according to the production method of an organic piezoelectric material will now further be detailed.

"Co-casting" may be any of a successive multi-layer casting method in which a 2-layer or 3-layer constitution is formed via different dies; a simultaneous multi-layer casting method in which a 2-layer or 3-layer constitution is formed via confluence in a die having 2 or 3 slits; and a multi-layer casting method in which successive multi-layer casting and simultaneous multi-layer casting are combined.

In the present invention, a "liquid in which an organic piezoelectric material is dissolved" represents the state where an organic piezoelectric material is dissolved in a dissolving medium (a solvent). Any appropriate additives such as a hardener, a plasticizer, and an antioxidant may be added to the organic piezoelectric material liquid. Of course, other additives may also be added as appropriate. The solid concentration in the organic piezoelectric material liquid is preferably 5-30% by mass, more preferably 10-25% by mass.

Solvents used in the present invention may be used individually or in combination. However, mixed use of a good solvent and a poor solvent is preferable from the viewpoint of production efficiency. With regard to a more preferable mixed ratio of the good solvent and the poor solvent, the good solvent is 70-99% by mass and the poor solvent is 30-1% by mass. As to the "good solvent" and the "poor solvent" used in the present invention, a solvent dissolving a used organic piezoelectric material on its own is defined as a good solvent and in contrast, a solvent swelling or not dissolving such a material on its own is defined as a poor solvent.

Therefore, the good solvent and the poor solvent are changed depending on the type and structure of an organic piezoelectric material. For example, when methyl ethyl ketone is used as a solvent, the solvent serves as a good solvent for PVDF and in contrast, results in serving as a poor solvent for a polyurea resin constituted of a diisocyanate compound such as 4,4'-diphenylmethane diisocyanate (MDI) and a diamine compound such as 4,4'-diaminodiphenylmethane (MDA).

As a good solvent used in the present invention, a solvent such as methyl ethyl ketone, and dimethylformamide, dimethylacetamide, dimethylformamide, and N-methylpyrrolidone are cited.

Further, as a poor solvent used in the present invention, for example, methanol, ethanol, n-butanol, cyclohexane, or cyclohexanone is preferably used.

When an organic piezoelectric material liquid is prepared, as a dissolving method of an organic piezoelectric material, any common method can be used. However, as a preferable method, a method is preferably employed in which an organic piezoelectric material is mixed with a poor solvent to be wetted or swollen and then mixed with a good solvent. In this case, to prevent occurrence of aggregated insoluble substances called gel or aggregated powdery mass, a method may be used in which heating is carried out for dissolution with stirring under pressure at the boiling point or more of a solvent at room temperature and also in a temperature range where the solvent does not boil. Pressurization may be carried out by a method in which an inert gas such as nitrogen gas is injected or by increasing the vapor pressure of the solvent via heating. Heating is preferably carried out from the outside. For example, those of jacket types are preferable for easier temperature control.

Heating temperature after solvent addition is preferably at least the boiling point a used solvent and also in a temperature range where the solvent does not boil. The temperature is preferably set at 40° C. or more and also in the range of 50-100° C. Further, pressure is controlled at a set temperature so as for the solvent not to boil.

After dissolution, removal from the container is carried out while cooling or extraction from the container is performed by a pump, followed by cooling using a heat exchanger for film formation. At this moment, the cooling temperature may be lowered to room temperature. However, cooling is more preferably carried out down to a temperature which is 5-10° C. lower than the boiling point to reduce the viscosity of an organic piezoelectric material liquid.

For example, in production of an organic piezoelectric material of at least 2 layers, an organic piezoelectric material of at least 2 layers can also be obtained as follows: an organic piezoelectric material liquid A prepared by mixing and dispersing, using an in-line mixer, an organic piezoelectric material liquid in which an organic piezoelectric material is dissolved in a solvent, particles, and a solution in which a small amount of the organic piezoelectric material is dissolved and an organic piezoelectric material liquid B in which the organic piezoelectric material is dissolved (other additives such as a cross-linking agent are separately added if appropriate) are co-cast (i.e. the casting step) using a die slit with a plurality of slits so that the organic piezoelectric material liquid A containing particles is cast directly on the casting belt; then a part of the solvent is removed by heating (i.e. the drying step on the casting belt); and thereafter peeling from the casting belt is carried out and the thus-peeled film is dried (i.e. the film drying step).

As the support in the casting step, a support in which belt- or drum-shaped stainless steel is mirror-finished is preferably used. The temperature of such a support in the casting step is in a common temperature range, and namely at a temperature of 0° C.-less than the solvent boiling point, casting can be carried out. However, casting onto the support of 0-60° C. is preferable to gel the dope and to extend the peeling limit duration. Casting onto the support of 5-40° C. is more preferable. The peeling limit duration is duration in which in the casting speed limit under which a transparent film exhibiting excellent flatness can be obtained continuously, a cast organic piezoelectric material liquid remains on the support. A sorter peeling limit duration is preferable for enhanced productivity.

The surface temperature of the support of the casting side is 10-80° C. and the temperature of the solution is 15-60° C. Further, the temperature of the solvent is preferably higher than that of the support by at least 0° C., and such setting is more preferably made at 5° C. or more. Higher solvent temperature and support temperature are preferable to increase the drying speed of the solvent. However, excessively higher temperatures may cause foam formation or flatness degradation. A more preferable range of the temperature of the support is 20-40° C. and a more preferable range of the solution temperature is 35-45° C. The support temperature during peeling is allowed to be preferably 10-40° C., more preferably 15-30° C., whereby the adhesion force between the organic piezoelectric material and the support can be reduced.

To allow an organic piezoelectric material during production to exhibit excellent flatness, the residual solvent amount during peeling from the support is preferably 1-80%, more preferably 3-40%, specifically preferably 5-30%.

In the present invention, the residual solvent amount is defined by the following expression.

Residual solvent amount=(mass prior to heating treatment−mass after heating treatment)/(mass after heating treatment)×100%

Herein, heating treatment in determination of the residual solvent amount refers to 1-hour heating treatment for an organic piezoelectric material at a certain temperature ranging from 100-200° C.

The peeling tension during peeling of an organic piezoelectric material from the support is commonly 20-25 kg/m for peeling. However, the organic piezoelectric material of the present invention is a thin film, whereby wrinkles tend to occur during peeling. Therefore, peeling is preferably carried out in the range of the minimum peelable tension −17 kg/m, more preferably the minimum tension −14 kg/m. Further, in the drying step of an organic piezoelectric material, the organic piezoelectric material having been peeled from the support is further dried, whereby the residual solvent amount therein is allowed to be preferably at most 3% by mass, more preferably at most 0.1% by mass.

In the drying step, a system is commonly employed in which an organic piezoelectric material is dried while conveyed using a roll suspension system or a pin tenter system. The organic piezoelectric material is preferably dried while the width thereof is maintained using the pin tenter system to enhance dimensional stability. Especially, immediately after peeling from the support, while the residual solvent amount is large, such width maintenance is specifically preferably carried out, whereby dimensional stability enhancement effects are further expressed. The member for drying is not specifically limited, and hot air, infrared radiation, a heating roll, or microwaves are commonly employed. In view of simplicity, hot air is preferably employed. The drying temperature is preferably divided into temperatures of 3-5 stages in the range of 30-200° C. and gradually raised. Drying in the range of 50-140° is more preferable to improve the dimensional stability.

(Organic Piezoelectric Film)

An organic piezoelectric film according to the present invention can be produced using the above piezoelectric material by any of the conventionally known methods such as a melting method and a casting method.

In the present invention, as the production method of such an organic piezoelectric film, employable is a method for forming a polymer film basically using a method in which a solution of the polymer material is coated onto a substrate and dried or a well-known solution polymerization coating method in which a raw material of the polymer material is used.

A specific method and condition of the solution polymerization coating method can be based on any of the well-known methods. For example, it is preferable to employ a method in which a mixed solution of raw materials is coated onto a substrate and dried to some extent under reduced pressure (the solvent is removed), and then heating and thermal polymerization are carried out. Thereafter or at the same time, polarization treatment is performed to form an organic piezoelectric film.

Herein, to enhance piezoelectric characteristics, it is useful to apply treatment to uniform the molecular arrangement. Such a method includes stretching film formation and polarization treatment.

As the stretching film formation method, various well-known methods are employable. For example, a liquid in which the above organic polymer material is dissolved in an organic solvent such as ethyl methyl ketone (MEK) is cast onto a substrate such as a glass plate and the solvent is dried at room temperature to obtain a film of a desired thickness. Then, this film is stretched to a length of a predetermined factor at room temperature. With regard to this stretching, stretching can be carried out in the uniaxial or biaxial direction to the extent that an organic piezoelectric film having a predetermined shape is not broken. The stretching factor is 2-10 times, preferably 2-6 times.

(Polarization Treatment)

As the polarization treatment method in polarization treatment according to the resent invention, a well-known method such as direct voltage application treatment, alternating voltage application treatment, or corona discharge treatment is applicable.

For example, in the case of the corona discharge treatment method, corona discharge treatment can be carried out using an apparatus incorporating a commercially available high voltage power source and electrodes.

Discharge conditions depend on the equipment and the treatment ambience. Therefore, such conditions are preferably selected appropriately. The voltage of the high voltage power source is preferably −1-20 kV, and the current and the electrode distance are preferably 1-80 mA and 1-10 cm, respectively. The applied voltage is preferably 0.5-2.0 MV/m.

As the electrodes, preferable are acicular electrodes, linear electrodes (wire electrodes), or net-shaped electrodes having been conventionally used. However, the present invention is not limited thereto.

When the organic piezoelectric material of the present invention is polarized by corona discharge, it is preferable that a flat surface electrode is placed so as to be brought into contact on a first surface of the organic piezoelectric material and also a columnar corona discharge electrode is placed on the second surface side opposed to the first surface to carry out polarization treatment by corona discharge.

The polarization treatment is preferably carried out via an embodiment in which the treatment is performed in the flow of nitrogen or a rare gas (helium or argon) under an ambience of a mass absolute humidity of at most 0.004 in order to prevent oxidation of the material surface caused by water and oxygen and in order not to impair piezoelectric properties. The treatment in the flow of nitrogen is specifically preferable.

Further, it is preferable that corona discharge is carried out while at least one of an organic piezoelectric material having a flat surface electrode placed so as to be in contact on the first surface and a columnar corona discharge electrode placed on the second surface side is moved at a certain rate.

Herein, in the present invention, the "mass absolute humidity" refers to the ratio SH (specific humidity) defined by the following expression, provided that the mass of dry air is $m_{DA}$ [kg] and the mass of water vapor contained in humid air is $m_W$ [kg]. The unit is represented by [kg/kg(DA)] (DA stands for dry air). However, in the present invention, expressions are made without this unit.

$$SH = M_W/M_{DA} [kg/kg(DA)] \quad \text{(Expression)}$$

Herein, air containing water vapor is referred to as "humid air" and air in which water vapor is eliminated from the humid air is referred to as "dry air."

Incidentally, the definition of the mass absolute humidity in the flow of nitrogen or a rare gas (helium or argon) is based on the above case of air and referred to as the ratio SH defined based on the above expression, provided that the mass of a dry gas is $m_{DG}$ [kg] and the mass of water vapor contained in a humid gas is $m_W$ [kg]. The unit is represented by [kg/kg(DG)] (DG stands for dry gas). However, in the present invention, expressions are made without this unit.

Further, "placement" means that an existing electrode having been previously produced separately is placed on the surface of an organic piezoelectric material so as to be brought into contact therewith, or that an electrode constituent material is bonded to the surface of an organic piezoelectric material by a deposition method to form an electrode on this surface.

Herein, it is preferable to form, under an electrical field in the formation process, an organic piezoelectric film which is formed using the organic piezoelectric material of the present invention, namely to carry out polarization treatment in the formation process. In this case, a magnetic field may be used in combination.

In a corona discharge treatment method according to the present invention, such treatment can be carried out using an apparatus incorporating a commercially available high voltage power source and electrodes.

Discharge conditions depend on the equipment and the treatment ambience. Therefore, such conditions are preferably selected appropriately. With regard to the voltage of the high voltage power source, the positive and the negative voltage are preferably 1-20 kV, and the current and the electrode distance are preferably 1-80 mA and 0.5-10 cm, respectively. The applied electrical field is preferably 0.5-2.0 MV/m. An organic piezoelectric material or an organic piezoelectric film in the polarization treatment is preferably kept in a temperature of 50-250° C., more preferably 70-180° C.

As an electrode used in corona discharge, a columnar electrode as described above needs to be used to carry out uniform polarization treatment.

Herein, in the present invention, the diameter of the circle of such a columnar electrode is preferably 0.1 mm-2 cm. The length of the column is preferably allowed to be an appropriate one depending on the size of an organic piezoelectric material to be polarized. For example, in general, from the viewpoint of uniform polarization treatment, the length is preferably at most 5 cm.

These electrodes are preferably in the stretched state at the portion where corona discharge is carried out, and such stretching can be realized by a method in which a certain load is applied to both end thereof or fixation is made in the state of applying a certain load. Further, as a constituent material of these electrodes, a common metal material is usable. However, gold, silver, and copper are specifically preferable.

A flat surface electrode placed so as to be in contact on the first surface is preferably kept in uniformly close contact with an organic piezoelectric material to carry out uniform polarization treatment. Namely, it is preferable to form an organic polymer film or an organic piezoelectric film on a substrate on which a flat surface electrode has been placed and thereafter to carry out corona discharge.

Herein, as a method for producing an ultrasonic oscillator according to the present invention, a production method of an embodiment is preferable in which polarization treatment is carried out prior to formation of electrodes placed on both sides of an organic piezoelectric (body) film, after electrode formation on one side, or after electrode formation on both sides. Further, the polarization treatment is preferably a voltage application treatment.

(Substrate)

With regard to the substrate, a substrate is selected depending on the intended purpose and usage of an organic piezoelectric body film according to the present invention. In the present invention, usable is a plastic plate or a film such as polyimide, polyamide, polyimideamide, polyethylene terephthalate (PET), polyethylene naphthalate (PEN), polymethyl methacrylate (PMMA), a polycarbonate resin, or a cycloolefin polymer. Further, those obtained by covering the surface of any of these materials with aluminum, gold, copper, magnesium, or silicon may be used. Still further, a plate or a film of an aluminum, gold, copper, magnesium, or silicon single body, or a single crystal of a rare earth halide. And, the substrate itself is not used in some cases.

(Ultrasonic Oscillator)

An ultrasonic oscillator according to the present invention is characterized by using an organic piezoelectric film formed using the organic piezoelectric material of the present invention. The ultrasonic oscillator is preferably allowed to be an ultrasonic receiving oscillator used in an ultrasonic medical diagnostic imaging device probe provided with an ultrasonic transmitting oscillator and an ultrasonic transmitting oscillator.

Incidentally, an ultrasonic oscillator is usually constituted by arranging a pair of electrodes so as to sandwich a layer (or a film) formed of a film-shaped piezoelectric material (a "piezoelectric film," a "piezoelectric body film," or a "piezoelectric body layer"), and then an ultrasonic probe is constituted for example, via one-dimensional arrangement of a plurality of such oscillators.

A predetermined number of such oscillators of the long axis direction arranged with a plurality of the oscillators are set as an aperture, and thereby a function is performed in which a plurality of the oscillators belonging to the aperture are driven; an ultrasonic beam is focused on and irradiated to a measurement portion in a tested subject; and also an ultrasonic reflective echo emitted from the tested subject is received by a plurality of the oscillators belonging to the aperture for conversion into an electrical signal.

An ultrasonic receiving oscillator and an ultrasonic transmitting oscillator according to the present invention will now be detailed.

<Ultrasonic Receiving Oscillator>

An ultrasonic receiving oscillator according to the present invention is a oscillator having an ultrasonic receiving piezoelectric material used for an ultrasonic medical diagnostic imaging device probe. A piezoelectric material constituting the oscillator is preferably an embodiment employing an organic piezoelectric film formed using the organic piezoelectric material of the present invention.

Herein, an organic piezoelectric material or an organic piezoelectric film used in an ultrasonic receiving oscillator preferably has a specific dielectric constant of 10-50 in the thickness resonance frequency. Adjustment of the specific dielectric constant can be carried out via adjustment of the number of the above substituent R possessed by a compound constituting the organic piezoelectric material or a polar functional group such as a $CF_2$ group or CN group, the composition, and the degree of polymerization, as well as via the above polarization treatment.

Further, an organic piezoelectric body film constituting the receiving oscillator of the present invention can be constituted by laminating a plurality of polymer materials. In this case, as such laminated polymer materials, other than the above polymer materials, the following polymer materials having relatively small specific dielectric constant can be combined.

Herein, in the following examples, each number in a parenthesis represents the specific dielectric constant of a polymer material (resin).

For example, usable is a methyl methacrylate resin (3.0), an acrylonitrile resin (4.0), an acetate resin (3.4), an aniline resin (3.5), an aniline formaldehyde resin (4.0), an aminoalkyl resin (4.0), an alkyd resin (5.0), nylon-6-6 (3.4), an ethylene resin (2.2), an epoxy resin (2.5), a vinyl chloride resin (3.3), a vinylidene chloride resin (3.0), a urea formaldehyde resin (7.0), a polyacetal resin (3.6), polyurethane (5.0), a polyester resin (2.8), polyethylene (low-pressure) (2.3), polyethylene terephthalate (2.9), a polycarbonate resin (2.9), a melamine resin (5.1), a melamine formaldehyde resin (8.0), cellulose acetate (3.2), a vinyl acetate resin (2.7), a styrene resin (2.3), styrene butadiene rubber (3.0), a styrol resin (2.4), or an ethylene fluoride resin (2.0).

Herein, the polymer materials having relatively small specific dielectric constant are preferably selected depending on the intended purposes to adjust piezoelectric characteristics or to provide physical strength for an organic piezoelectric body film.

<Ultrasonic Transmitting Oscillator>

An ultrasonic transmitting oscillator according to the present invention is preferably constituted of a piezoelectric body material having an appropriate specific dielectric constant in view of the relationship with a oscillator incorporating the above receiving piezoelectric material. Further, a piezoelectric material exhibiting excellent heat resistance and voltage resistance is preferably used.

As an ultrasonic transmitting oscillator constituent material, various well-known organic piezoelectric materials and inorganic piezoelectric materials can be used.

As such an organic piezoelectric material, a polymer material similar to the above ultrasonic receiving oscillator constituent organic piezoelectric material can be used.

As such an inorganic material, usable is crystal, lithium niobate ($LiNbO_3$), potassium niobate tantalate [K(Ta, Nb)$O_3$], barium titanate ($BaTiO_3$), lithium tantalate ($LiTaO_3$), lead titanate zirconate (PZT), strontium titanate ($SrTiO_3$), or barium strontium titanate (BST). Herein, PZT is preferably $Pb(Zr_{1-n}Ti_n)O_3$ ($0.47 \leq n \leq 1$).

<Electrode>

A piezoelectric (body) oscillator according to the present invention is produced in such a manner that an electrode is formed on both sides or one side of a piezoelectric body film (layer) and the piezoelectric body film is polarized. When an ultrasonic receiving oscillator employing an organic piezoelectric material is produced, the above first surface electrode having been used in polarization treatment can be used as such. The electrode is formed using an electrode material mainly containing gold (Au), platinum (Pt), silver (Ag), palladium (Pd), copper (Cu), nickel (Ni), Tin (Sn), or aluminum (Al).

In formation of an electrode, initially, a base metal such as titanium (Ti) or chromium (Cr) is formed into a thickness of 0.02-1.0 μm by a sputtering method, and thereafter a metal mainly containing the above metal element and a metal material containing an alloy thereof, as well as partially an insulating material if appropriate are formed into a thickness of 1-10 μm using a sputtering method, a deposition method, or another appropriate method. Such electrode formation can be carried out, other than the sputtering method, via screen printing, a dipping method, or a spraying method using an electrically conductive paste prepared by mixing fine-powdered metal powder with low-boiling point glass.

Further, a predetermined voltage is supplied between the electrodes formed on both sides of a piezoelectric body film and thereby the piezoelectric body film is polarized to obtain a piezoelectric element.

(Ultrasonic Probe)

An ultrasonic probe according to the present invention is an ultrasonic medical diagnostic imaging device probe provided with an ultrasonic transmitting oscillator and an ultrasonic receiving oscillator, and has such a feature that the ultrasonic receiving oscillator of the present invention is used as a receiving oscillator.

In the present invention, only a single oscillator may play a role for both transmission and reception of ultrasonic waves. However, more preferably, oscillators for transmission and reception are separately constituted in a probe.

As a piezoelectric material constituting a receiving oscillator, a well-known ceramics inorganic piezoelectric material or organic piezoelectric material can be used.

In an ultrasonic probe according to the present invention, the ultrasonic receiving oscillator of the present invention can be arranged on or in parallel to a transmitting oscillator.

As a more preferred embodiment, a constitution is preferable in which the ultrasonic receiving oscillator of the present invention is laminated on an ultrasonic transmitting oscillator. In this case, the ultrasonic receiving oscillator of the present invention may be laminated on a transmitting oscillator via attachment on another polymer material (the above polymer (resin) film of relatively small specific dielectric constant serving as a support, for example, polyester film). In such a case, the thickness of the receiving oscillator and such another polymer material in total preferably corresponds to a preferable receiving frequency band from the viewpoint of probe designing. In view of a practical ultrasonic medical diagnostic imaging device and an actual frequency band for living body information gathering, the thickness is preferably 40-150 μm.

Incidentally, a backing layer, an acoustic matching layer, and an acoustic lens may be arranged for the probe. Further, a probe may be formed in which oscillators having a large number of piezoelectric materials are arranged two-dimensionally. A constitution as a scanner may be employed to sequentially scan a plurality of two-dimensionally-arranged probes for imaging.

(Ultrasonic Medical Diagnostic Imaging Device)

Figure 2:
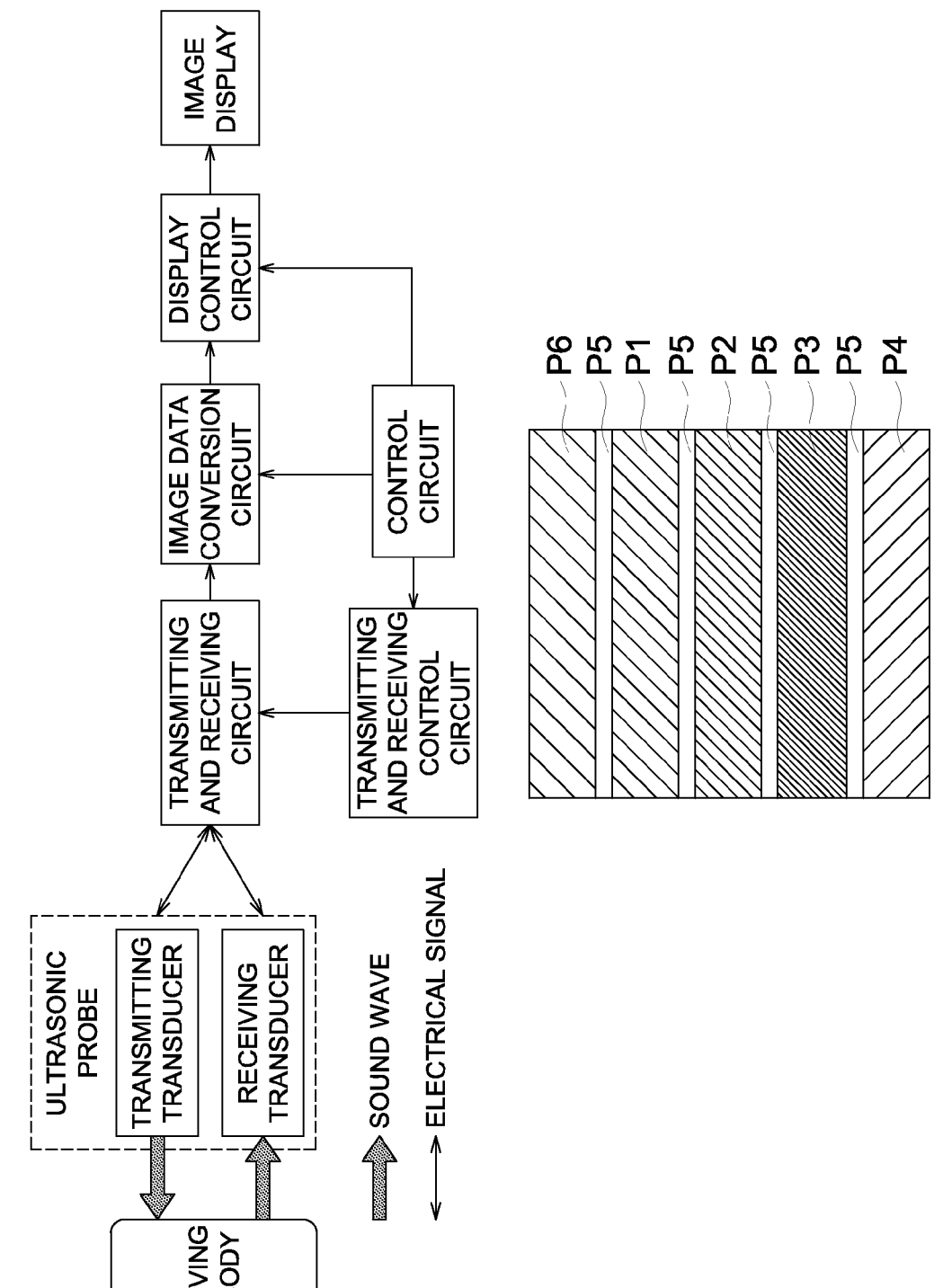
FIG. 2 is a schematic view showing the constitution of the main section of an ultrasonic medial diagnostic imaging device.
Figure 3:
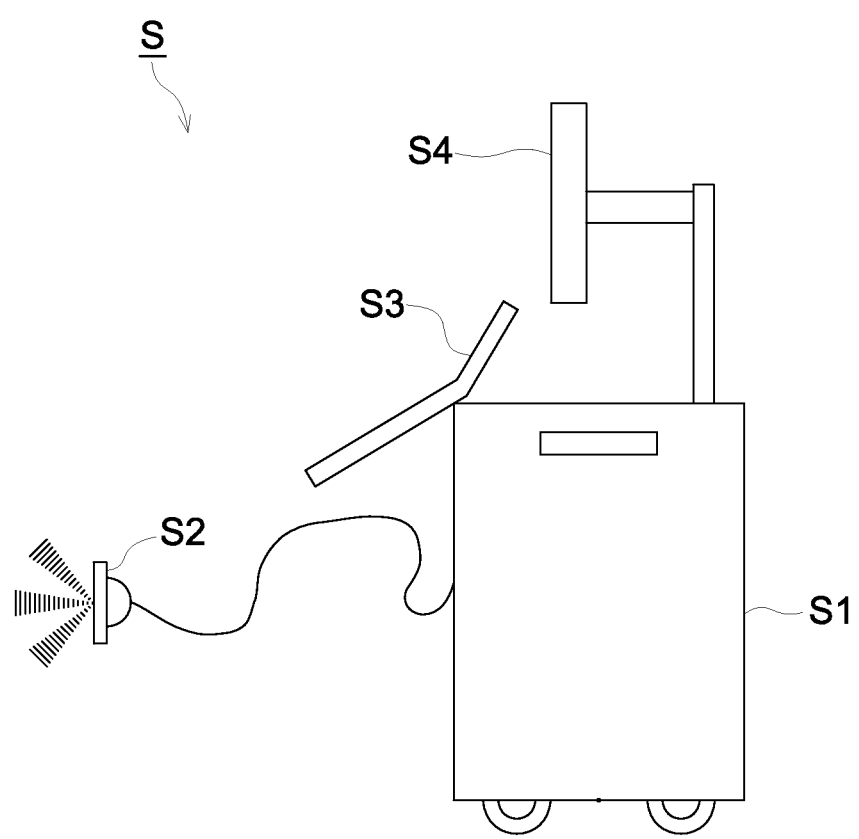
FIG. 3 is an external constitutional view of an ultrasonic medial diagnostic imaging device.

The ultrasonic probe of the present invention can be used for ultrasonic diagnostic systems of various embodiments, being preferably able to be used, for example, in the ultrasonic medial diagnostic imaging devices shown in FIG. 2 and FIG. 3.

FIG. 2 is a schematic view showing the constitution of the main section of an ultrasonic medial diagnostic imaging device of the embodiment of the present invention. This ultrasonic medical diagnostic imaging device is provided with an ultrasonic probe arranged with piezoelectric body oscillators to transmit an ultrasonic wave to a tested subject such as a patient and to receive the ultrasonic wave having been reflected from the tested subject as an echo signal. Further, provided are a transmitting and receiving circuit to generate an ultrasonic wave by supplying an electrical signal to the ultrasonic probe and also to receive an echo signal having been received by each piezoelectric body oscillator of the ultrasonic probe; and a transmitting and receiving control circuit to carry out transmitting and receiving control of the transmitting and receiving circuit.

Further, an image data conversion circuit to convert an echo signal received by the transmitting and receiving circuit into ultrasonic image data of the tested subject is provided. Still further, a display control circuit to carry out displaying by controlling the monitor using ultrasonic image data converted by the image data conversion circuit and a control circuit to control the entire ultrasonic medical diagnostic imaging device are provided.

The control circuit is connected to the transmitting and receiving control circuit, the image data conversion circuit, and the display control circuit, and the control circuit controls the behavior of each section. An electrical signal is applied to each piezoelectric body oscillator of an ultrasonic probe and thereby an ultrasonic wave is transmitted to the tested subject. Thereafter, a reflective wave generated via acoustic impedance mismatching is received by the ultrasonic probe.

Herein, the above transmitting and receiving circuit corresponds to a "member to generate an electrical signal" and the image data conversion circuit corresponds to an "image processing member."

According to the ultrasonic diagnostic system described above, an ultrasonic image having enhanced image quality, as well as enhanced reproducibility and stability thereof can be obtained compared with the prior art, utilizing the feature of the ultrasonic receiving oscillator of the present invention having excellent piezoelectric characteristics and heat resistance and being suitable for a high frequency/broad band.

EXAMPLES

The present invention will now specifically be described with reference to examples that by no means limit the scope of the present invention. Herein, in the following description, with regard to the amount of a compound, the unit "%" represents a relative amount based on 100% of the mass of a reference substance.

Example 1

Preparation of Hollow Particle Dispersion (1)

In a 3 L reaction vessel were added 10% of dodecyl mercaptan, 95% of styrene, 5% of dimethylaminopropyl acrylamide, 1,000% of ion exchange water, 1% of AIBA (2,2-azobis (2-amidinopropane) hydrochloride) and 1% of dodecyl trimethyl ammonium chloride. The mixture was allowed to polymerize at 70° C. for 8 hours to obtain a latex dispersion having an average particle diameter of 80 nm (CV value of 10%). By using this latex as seed particles, 10% of this latex as a solid content, 2% of dodecyl trimethyl ammonium chloride and 1% of AIBA were dispersed in 900% of ion exchange water. To the dispersion were added a mixture of 40% of methyl methacrylate, 20% of glycidyl methacrylate, 30% of styrene and 10% of divinylbenzene. The mixture was stirred at room temperature for 48 hours. Almost all of the above-described substances was absorbed by the seed particles. Then, when these were polymerized at 60° C. for 6 hours, a dispersion of hollow particles PP-1 was obtained having an average particle diameter of 180 nm (CV value of 10%). When this particle dispersion liquid was dried and was observed with TEM, the center section of the particles was transparent and the inside diameter was 90 nm (hollow ratio: 12.5%). Moreover, the glass transition temperature (Tg) of these particles was 107° C. The dispersion liquid of these hollow particles PP-1 was substituted with methyl ethyl ketone by centrifugation to obtain a methyl ethyl ketone dispersion liquid (1) of hollow particles PP-1.

Preparation of Hollow Particle Dispersion (2)

In a 2 L reaction vessel were added, in advance, 109.5% of water as a medium, 0.2 part of sodium benzene sulfonate (product name: F65, made by Kao Co., Ltd.) as an emulsifying agent and 0.5% of sodium persulfate as a polymerization initiator. On the other hand, 90% of methyl methacrylate, 10% of methacrylic acid, 0.5% of octylthio glycolate as a molecular weight controlling agent, 0.5% of an emulsifying agent (product name: F65, made by Kao Co., Ltd.) and 40% of water were mixed with stirring to obtain a water dispersion of mixed monomers. 20% of the water dispersion of mixed monomers was supplied to the above-described reaction vessel. The liquid in the reaction vessel was heated to 75° C. with stirring and a polymerization reaction was performed for 1 hour. Then, with keeping the temperature at 75° C., the remaining water dispersion of mixed monomers was continuously added to the reaction vessel over 2 hours. Further, digestion was performed for 2 hours to obtain a water dispersion of the seed particles having a solid content of 40%, an average particle diameter of 200 nm and a weight average molecular weight of 70,000.

In a 2 L reaction vessel was added, in advance, 240% of water as a medium. To this were added 15% of the above-described water dispersion of the seed particles as a solid content (48.4% of the water dispersion), 20% of styrene, 0.4% of sodium persulfate as a polymerization initiator. On the other hand, 69.5% of styrene, 10% of methacrylic acid, 0.5% of octylthio glycolate as a molecular weight controlling agent, 0.1% of an emulsifying agent (product name: F65, made by Kao Co., Ltd.) and 40% of water were mixed with stirring to obtain a water dispersion of mixed monomers. Then, the liquid in the reaction vessel was heated to 80° C. with stirring and a polymerization reaction of styrene was performed for 30 minutes to obtain polymer particles composed of polymerized styrene of seed particles. Subsequently, the liquid in the reaction vessel was kept at 80° C. with stirring, and the above-described water dispersion of mixed monomers was continuously added to the reaction vessel over 4 hours. 2 hours after the start of the addition of the water dispersion of mixed monomers in the reaction vessel, 0.5% of acrylic acid was added in one lot to copolymerize with styrene. Further, immediately after complete addition of the water dispersion of mixed monomers, 5% of divinylbenzene and 5% of styrene were added in one lot to obtain core-shell structured polymer particles which were produced by polymerization of styrene, acrylic acid, and divinylbenzene and lamination the polymer on the outermost layer of seed particles. About 15 minutes after adding all of the monomers, 5% of 25% ammonium hydroxide was added in one lot with stirring followed by heating to 90° C. and digested for 2 hours with stirring. The ratio of the unreacted monomers to the whole monomers before adding 25% ammonium hydroxide was 7%. Then, 0.3% of t-butyl hydroperoxide and 0.1% of formaldehyde resin were added in the reaction vessel. They were kept stirring for 1 hour to obtain a dispersion of hollow particles PP-2 having a solid content of 26.5% with an average particle diameter of 1,050 nm (CV: 10%). When this dispersion liquid was dried similarly and was observed with TEM, the particle had a single hole with an inside diameter of 860 nm. Moreover, the glass transition temperature (Tg) of these particles was 109° C. The dispersion liquid of these hollow particles PP-2 was substituted with methyl ethyl ketone by centrifugation to obtain a methyl ethyl ketone dispersion liquid (2) of hollow particles PP-2.

Preparation of Hollow Particle Dispersion (3)

To 2.0 L of calcium oxide slurry having a solid content of 7.5% and adjusted the liquid temperature of 15° C. was introduced a carbon dioxide gas with stirring at a rate of 1.5 L/minute for 2 hours to deposit calcium carbonate. Subsequently, the liquid temperature was raised to 80° C. and digestion was performed with stirring for 24 hours. When the produced calcium carbonate was observed with TEM, the primary particle diameter was found to be 40 to 80 nm. After making the above-mentioned calcium carbonate slurry into a water containing cake having of a water content of 65% with a centrifugal dehydrator, 22 g of this water containing cake was placed in 450 g of ethanol, followed by subjected to ultrasonic irradiation to disperse calcium carbonate in ethanol. To the dispersion were added 21 g of a 28% aqueous ammonia solution and 7.5 g of tetraethoxysilane, then stirring was continued for 12 hours, and calcium carbonate coated with silica was prepared. (Here, the volume ratio of tetraethoxysilane/ethanol was 0.01, the content of $NH_3$ contained in the aqueous ammonia solution was 9.3 mol per 1 mol of tetraethoxysilane, and the content of water was 30 mol with respect to 1 mol of tetraethoxysilane.) The prepared product was observed with TEM and an outer diameter of the particles was 90 nm. Subsequently, after removing liquid in the slurry of calcium carbonate coated with silica with suction filtration, washing was carried out with 1,200 ml of ethanol and 1,200 ml of water. Then the calcium carbonate was dispersed again in 800 ml of water. To the water dispersion was added 200 ml of 2.5 mol/L of HCl (acid concentration of the whole liquid was 0.5 mol/L), and the mixture was stirred for 1 hour to dissolve calcium carbonate. When the product was observed with TEM, it was confirmed that silica hollow particles had a primary particle diameter of 90 nm (CV: 15%), and an inside diameter was 80 nm. The dispersion liquid of these hollow particles PP-3 was substituted with dimethylformamide by centrifugation to obtain a dimethylformamide dispersion liquid (3) of hollow particles PP-3.

Preparation of Hollow Particle Dispersion (4)

To 4.0 kg of kerosene were mixed 1.0 kg of secondary deposition Shirasu, which is a natural deposit of volcanic glass and produced in Yoshida-cho, Kagoshima prefecture, and 35.5 g of $Na_2SO_4$. Further, 100 g of HOMOGENOL L1820 which is an anionic surfactant made by Kao Co., Ltd.

was added to obtain a slurry. A raw slurry was obtained by carrying out wet grinding of this slurry with a media stirring type mill. The used media stirring type mill had an internal volume of 1,400 ml and the composing material was made from zirconia. The glass beads made of zirconia with an average diameter of 0.65 mm were put in the mill in an amount of 1,120 ml and used. The operating condition was 2,500 rpm in rotational frequency, and carried out wet grinding for 30 minutes. When the finely grinded Shirasu was collected from the obtained raw slurry and SEM observation was carried out, the average particle diameter was found to be 0.6 μm. The obtained raw shiny was sprayed from the two fluid nozzles, and it was ignited with a pilot burner to perform atomized firing. Thus, hollow glass spherical bodies were manufactured. The hollow glass spherical bodies were recovered with a bag filter and it was mixed with water. The water float rate was measured by collecting the material with centrifugation separation. As a result, it was confirmed that about 30 weight % of the material was floated on the surface of water. After collecting the hollow glass spherical bodies which floated on the water surface, the average particle diameter was measured. It was found that the average particle diameter was 9.7 μm. These particles were distributed into dimethylformamide, and a dispersion liquid (4) of hollow particles PP-4 was prepared.

Example 2

Preparation of Added Liquid (1)

Six percent of PVDF-3FE and at least 140% of methyl ethyl ketone were placed into a sealed container, and the resulting mixture was completely dissolved while heated and stirred and then filtered. Ten percent of the hollow particle dispersion (1) was added to the resulting product with stirring, followed by stirring for 30 minutes and filtration to prepare an added liquid (1).

In the same manner, an added liquid (2) and an added liquid (3) were prepared from the hollow particle dispersion (2) and the hollow particle dispersion (3), respectively. Herein, with regard to the molecular weight of the used PVDF, the weight average molecular weight was 100,000 and Mn/Mw was 2.6 as the results of GPC determination under the following conditions.

Solvent: 30 mM of LiBr in N-methylpyrrolidone
Apparatus: HCL-8220GPC (made by Tosoh Co., Ltd.)
Column: TSKgel Super AWM-H×2 (made by Tosoh Co., Ltd.)
Column temperature: 40° C.
Sample concentration: 1.0 g/L
Injection amount: 40 μl
Flow rate: 0.5 ml/minute
Calibration curve: using a calibration curve prepared based on 9 samples of Standard polystyrene (PS-1, made by Polymer Laboratories Co., Ltd.) having Mw of 580 to 2,560,000.

(Production of Organic Piezoelectric Material Liquid A)

One hundred percent of PVDF-3FE and 400% of methyl ethyl ketone were placed into a sealed container. The resulting mixture was completely dissolved while heated and stirred, followed by filtration to prepare an organic piezoelectric material liquid A.

(Production of Organic Piezoelectric Material Liquid B)

Under nitrogen ambience, the macromonomer M-31 was dissolved in N-methylpyrrolidone at room temperature. The macromonomer M-35 having been dissolved in N-methylpyrrolidone was added thereto and then the reaction solution was heated up to 80° C. and stirred for 3 hours. The thus-obtained reaction solution was filtered to prepare an organic piezoelectric material liquid B. Herein, the molecular weight was determined using GPC under the above conditions, whereby the weight average molecular weight was 34,000 and Mw/Mn was 4.3.

(Production of Organic Piezoelectric Material Liquid C)

Under nitrogen ambience, a macromonomer, 2,2-bis(4-aminophenyl)hexafluoropropane was dissolved in DMSO at room temperature. Benzophenone-4,4'-diisothiocyanic acid having been dissolved in DMSO was added thereto and then the reaction solution was heated up to 80° C. and stirred for 3 hours. The thus-obtained reaction solution was filtered to prepare an organic piezoelectric material liquid C.

Under the same conditions as for the organic piezoelectric material B, the molecular weight was determined using GPC, whereby the weight average molecular weight was 23,000 and Mw/Mn was 3.6.

(Production of Organic Piezoelectric Materials)

An added liquid was added to 100% of the organic piezoelectric material liquids A or B at the amount described in Table 1. Each resulting mixture was sufficiently mixed using an in-line mixer (static in-line mixer Hi-Mixer, SWJ, produced by Toray Industries, Inc.) and filtered. Subsequently, using a belt casting apparatus, confluence was made in a die to form one layer structure. Then, the liquid was uniformly cast at 33° C. having a width of 1,000 mm on a stainless steel casting belt. The solvent was evaporated until the residual solvent amount reached 25% on the stainless steel casting belt, and peeling from the casting belt was carried out at a peeling tension of 13 kg/m. The thus-peeled organic piezoelectric material was slit to a width of 700 mm, and then drying was terminated while conveyed in the drying zone with rolls to carry out slitting to a width of 500 mm. Thereby, laminated samples were produced by changing the added liquid and the casting film thickness, as well as the heat treatment conditions, as described in Table 1. Further, in casting of the organic piezoelectric material liquid, the die was switched to a single layer casting die to produce a single layer sample in the same manner using the added liquid A of Sample 1 of the present invention.

The vacuum evaporation application of aluminum was carried out by vacuum evaporation system JEF-420 (product made from JEOL Ltd. Datum) so that the surface resistivity of both sides of the prepared sample might become 1Ω or less. Thus a sample provided with a surface electrode was obtained. Subsequently, polarization treatment was carried out by applying the alternating voltage of 0.1 Hz to this electrode at room temperature. The polarization treatment was performed from low voltage by increasing the applied voltage gradually until the electric field between the electrodes became 50 MV/m. Thus a sample of an organic piezoelectric material of the present invention was obtained.

In addition, the samples each using an organic piezoelectric materials B and C were heated to 200° C. at a rate of 5° C./minute with keeping the applied electric field of 100 MV/m using a high voltage power supply apparatus HARB-20R60 (Matsusada Precision Inc.). After holding for 15 minutes at 200° C., it was gradually cooled to room temperature with keeping the applied voltage, thus polling processing was performed.

<Adhesion Properties>

After deposition coating, the sample was left stand at 23° C. under a humidity of 55% for 24 hours, and then adhesion of the surface electrode thereof was examined by a grid tape peeling test based on JIS D0202-1988. A cellophane tape ("CT24" produced by Nichiban Co., Ltd.) was allowed to adhere to a film using the ball of a finger, followed by peeling. Judgment was conducted by the number of grids having not been peeled among 100 grids. The case of no peeling was expressed as 100/100 and in contrast, the case of complete peeling was expressed as 0/100.

JEITA EM-4501 (formerly EMAS-6100) (set by Japan Electronics & Information Technology Industries Association) concerning the electrical testing method of a piezoelectric ceramic oscillator.

The various evaluation results are collectively listed in Table 1.

TABLE 1

| | First layer | | | | | | Electro- | | | |
|---|---|---|---|---|---|---|---|---|---|---|
| | Organic piezo- | In-line added liquid | | Dry thickness | Stretching | | | Piezoelectric e constant | | mechanical coupling |
| Sample No. | electric material liquid | Dispersion | Added amount (weight %) | after casting (μm) | (thickness after stretching) | Heat treatment (temperature/ time) | Adhesion properties | (relative value) | | coefficient |
| | | | | | | | | Room temperature | 100° C. | Room temperature | Remarks |
| 1 | A | PP-1 | 10 | 40 | None | 135 | 72% | 126% | 109% | 0.2 | Inv. |
| 2 | A | PP-1 | 20 | 40 | None | 135 | 82% | 132% | 114% | 0.3 | Inv. |
| 3 | A | PP-1 | 20 | 100 | Done (40 μm) | 135 | 88% | 145% | 114% | 0.3 | Inv. |
| 4 | A | PP-1 | 40 | 40 | None | 135 | 85% | 140% | 113% | 0.2 | Inv. |
| 5 | A | PP-1 | 60 | 40 | None | 135 | 83% | 126% | 105% | 0.2 | Inv. |
| 6 | A | PP-2 | 20 | 40 | None | 145 | 85% | 128% | 116% | 0.3 | Inv. |
| 7 | A | PP-2 | 20 | 40 | None | 125 | 88% | 131% | 118% | 0.2 | Inv. |
| 8 | A | PP-2 | 20 | 100 | Done (40 μm) | 145 | 87% | 142% | 115% | 0.3 | Inv. |
| 9 | A | PP-3 | 20 | 40 | None | 135 | 78% | 132% | 111% | 0.2 | Inv. |
| 10 | A | PP-4 | 20 | 40 | None | 135 | 78% | 121% | 101% | 0.2 | Inv. |
| 11 | B | PP-1 | 20 | 40 | None | 135 | 85% | 129% | 112% | 0.2 | Inv. |
| 12 | B | PP-2 | 20 | 40 | None | 135 | 28% | 128% | 112% | 0.2 | Inv. |
| 13 | B | PP-3 | 20 | 40 | None | 135 | 32% | 133% | 103% | 0.2 | Inv. |
| 14 | A | PP-1 PP-2 | 20 10 | 40 | None | 135 | 87% | 131% | 106% | 0.2 | Inv. |
| 15 | A | PP-1 PP-3 | 20 20 | 40 | None | 135 | 89% | 131% | 133% | 0.3 | Inv. |
| 16 | C | PP-1 | 20 | 40 | None | 135 | 89% | 135% | 125% | 0.3 | Inv. |
| 17 | A | — | — | 40 | None | 135 | 10% | 110% | 91% | 0.2 | Comp. |
| 18 | PVDF | — | — | 100 | Done (40 μm) | None | 0% | 100% | 68% | 0.1 | Comp. |
| 19 | A | Comp.-1 | 20 | 40 | None | 135 | 56% | 105% | 73% | 0.1 | Comp. |

PVDF: polyvinylidene fluoride (molecular weight Mw: 250,000)
Comparison-1: dispersion of cross-linked polystyrene particles (100 nm)

<Piezoelectricity>

Lead wires were attached to electrodes of both sides of the thus-obtained sample to which the electrodes have been attached. Then, with regard to the sample under an ambience of 25° C. and having been heated up to 100° C., using impedance analyzer 4294A (produced by Agilent Technologies), evaluation was conducted on piezoelectric e constant and electromechanical coupling coefficient using thickness resonance wavelength. The results are listed in Table 1. Herein, the piezoelectric e constant is expressed as a relative value in which the value of a comparative PVDF film determined at room temperature is designated as 100%. Incidentally, in the present invention, the "piezoelectric e constant" is one of the coefficients expressing piezoelectric characteristics, indicating stress generated when an electrical field is applied to a piezoelectric body.

In determination, 600-point frequency sweeping was carried out from 40 Hz-110 MHz at regular intervals to determine the value of specific dielectric constant in the thickness resonance frequency. In the same manner, the electromechanical coupling coefficient was determined from peak frequency P of a resistance value and peak frequency S of a conductance value in the vicinity of the thickness resonance frequency. Further, the piezoelectric e constant was determined from these numerical values. The determination method was based on item 4.2.6 with respect to the thickness vertical vibration of a disc oscillator described in Standard The results shown in Table 1 clearly show that the performances such as such as adhesion properties and piezoelectricity are superior to that of the comparative examples, whereby excellent heat resistance is specifically expressed.

Example 3

Production and Evaluation of an Ultrasonic Probe)

<Production of Transmitting Piezoelectric Materials>

$CaCO_3$, $La_2O_3$, $Bi_2O_3$, and $TiO_2$ as component raw materials and MnO as an auxiliary component raw material were prepared. The component raw materials were weighed to allow the final component composition to be $(Ca_{0.97}La_{0.03})Bi_{4.01}Ti_4O_{15}$. Subsequently, pure water was added thereto and the resulting mixture was mixed for 8 hours using a ball mill containing zirconia media in pure water, followed by being sufficiently dried to obtain mixed powder. The thus-obtained mixed powder was tentatively shaped, followed by being tentatively fired in air at 800° C. for 2 hours to produce a tentatively fired substance. Thereafter, pure water was added to the thus-obtained tentatively fired substance, followed by fine pulverization using a ball mill containing zirconia media in pure water and by drying to produce piezoelectric ceramics raw material powder. In such fine pulverization, the duration for fine pulverization and fine pulverization conditions were varied, whereby piezoelectric ceramics raw material powders each having a particle diameter of 100 nm were obtained. Pure water serving as a binder was added to each of the piezoelectric ceramics raw material powders of different particle diameter at 6% by mass and the resulting mixture was press-shaped to give a plate-like tentatively shaped body of a thickness of 100 μm. This plate-like tentatively shaped body was vacuum-packed and then shaped using a press by applying a pressure of 235 MPa. Subsequently, the above shaped body was fired. Thus, a fired body having a thickness of 20 μm as the final fired body was obtained. Herein, each firing temperature was 1100° C. Then, polarization treatment was carried out by applying an electrical field of at least 1.5×Ec (MV/m).

(Production of Receiving Laminated Oscillators)

Using the organic piezoelectric material of No. 9 produced in Example 2, a receiving laminated oscillator was laminated on the above transmitting piezoelectric material based on a common method, and also a backing layer and an acoustic coupling layer were placed to experimentally produce an ultrasonic probe.

Incidentally, a probe was produced as a comparative example in the same manner as for the above ultrasonic probe except that instead of the receiving laminated oscillator, a receiving laminated oscillator only employing a polyvinylidene fluoride film (an organic piezoelectric body film) was laminated on the receiving laminated oscillator. Subsequently, the receiving sensitivity and the insulation breakdown strength of 2 types of the ultrasonic probes were determined for evaluation.

Herein, with regard to the receiving sensitivity, the basic frequency f1 of 5 MHz was transmitted and then relative receiving sensitivity was determined at 10 MHz as the receiving secondary harmonic f2, at 15 MHz as the tertiary harmonic, and at 20 MHz as the quaternary harmonic. The relative receiving sensitivity was determined using acoustic strength measurement system Model 805 (1-50 MHz) (produced by Sonora Medical System, Inc., 2021 Miller Drive, Longmont, Colo. (0501, USA)). In determination of the insulation breakdown strength, load power P was increased fivefold and 10-hour testing was conducted. Then, the load power was returned to the reference to evaluate the relative receiving sensitivity. The evaluation was made as follows: a sensitivity decrease of at most 1% prior to the load test was designated as excellent; a decrease from more than 1%—less than 10% was designated as acceptable; and a decrease of at least 10% was designated as poor.

The above evaluation confirmed that the probe provided with a receiving piezoelectric (body) laminated oscillator according to the present invention had twice the relative receiving sensitivity of the comparative example, and also exhibited excellent insulation breakdown strength. Namely, the ultrasonic receiving oscillator of the present invention was confirmed to be suitably able to be employed for a probe used in an ultrasonic medical diagnostic imaging device as described in FIG. 1.

The invention claimed is:

1. A method for producing an ultrasonic oscillator, comprising: the step of carrying out a polarization treatment to an organic piezoelectric material wherein the organic piezoelectric material comprises hollow particles having an average particle diameter of 10 μm or less,
the hollow particles are made of at least one resin selected from the group consisting of a polystyrene resin, an acrylic resin, a styrene acrylic resin, a polyethylene resin, a polypropylene resin, a polyacetal resin, a chlorinated polyether resin, polyvinyl chloride resin, a phenol-formaldehyde resin, a urea-formaldehyde resin, a melamine-formaldehyde resin, a furan resin and an unsaturated polyester resin, and the polarization treatment is carried out at one of the moments of:
before providing two electrodes on both surfaces of the organic piezoelectric material;
after providing one of the two electrodes on one of the surfaces of the organic piezoelectric material; and
after providing the two electrodes on the both surfaces of the organic piezoelectric material.

2. The method for producing the ultrasonic oscillator of claim 1, wherein the polarization treatment is a voltage applying treatment or a corona discharge treatment.

3. The method of claim 1, wherein the organic piezoelectric material, further comprising:
an organic polymer which contains vinylidene fluoride as a main component, or
an organic polymer which contains a compound having a urea bond or a thiourea bond in the molecule.

4. The method of claim 1, wherein the organic piezoelectric material has an electromechanical coupling coefficient thereof of 0.3 or more.

5. An ultrasonic probe comprising an ultrasonic transmitting oscillator and an ultrasonic receiving oscillator, wherein the ultrasonic transmitting oscillator or for the ultrasonic receiving oscillator comprises an ultrasonic oscillator produced using an organic piezoelectric material, wherein the organic piezoelectric material comprises hollow particles having an average particle diameter of 10 μm or less,
the hollow particles are made of at least one resin selected from the group consisting of a polystyrene resin, an acrylic resin, a styrene acrylic resin, a polyethylene resin, a polypropylene resin, a polyacetal resin, a chlorinated polyether resin, polyvinyl chloride resin, a phenol-formaldehyde resin, a urea-formaldehyde resin, a melamine-formaldehyde resin, a furan resin and an unsaturated polyester resin.

6. The probe of claim 5, wherein the organic piezoelectric material further comprising:
an organic polymer which contains vinylidene fluoride as a main component, or
an organic polymer which contains a compound having a urea bond or a thiourea bond in the molecule.

7. The probe of claim 5, wherein the organic piezoelectric material has an electromechanical coupling coefficient thereof of 0.3 or more.

8. An ultrasonic medical diagnostic imaging device comprising:
an electric signal emitting circuit;
an ultrasonic probe provided with a plurality of oscillators which emit an ultrasonic wave to a test object after receiving the electric signal, and produce a received signal corresponding to a reflected wave from the test object; and
an image processing circuit which produces an image of the test object by using the received signal produced by the ultrasonic probe,
wherein the ultrasonic probe is provided with an ultrasonic transmitting oscillator and an ultrasonic receiving oscillator, and at least one of the ultrasonic transmitting oscillator and the ultrasonic receiving oscillator is an ultrasonic oscillator produced with an organic piezoelectric material wherein the organic piezoelectric material comprises hollow particles having an average particle diameter of 10 μm or less,
the hollow particles are made of at least one resin selected from the group consisting of a polystyrene resin, an acrylic resin, a styrene acrylic resin, a polyethylene resin, a polypropylene resin, a polyacetal resin, a chlorinated polyether resin, polyvinyl chloride resin, a phenol-formaldehyde resin, a urea-formaldehyde resin, a melamine-formaldehyde resin, a furan resin and an unsaturated polyester resin.

9. The device of claim 8, wherein the organic piezoelectric material further comprising:
  an organic polymer which contains vinylidene fluoride as a main component, or
  an organic polymer which contains a compound having a urea bond or a thiourea bond in the molecule.

10. The device of claim 8, wherein the organic piezoelectric material has an electromechanical coupling coefficient thereof of 0.3 or more.

\* \* \* \* \*